US012571001B2

(12) United States Patent
Xiao et al.

(10) Patent No.: US 12,571,001 B2
(45) Date of Patent: Mar. 10, 2026

(54) BACULOVIRUS VECTOR AND USE THEREOF IN PREPARATION OF RECOMBINANT ADENO-ASSOCIATED VIRUS (rAAV) IN INSECT CELL

(71) Applicant: GENEVOYAGER (WUHAN) CO., LTD., Wuhan (CN)

(72) Inventors: He Xiao, Wuhan (CN); Xiaobin He, Wuhan (CN); Gang Huang, Wuhan (CN); Ying Hu, Wuhan (CN); Xing Pan, Wuhan (CN); Mengdie Wang, Wuhan (CN); Liang Du, Wuhan (CN)

(73) Assignee: GENEVOYAGER (WUHAN) CO., LTD., Wuhan (CN)

( * ) Notice: Subject to any disclaimer, the term of this patent is extended or adjusted under 35 U.S.C. 154(b) by 0 days.

(21) Appl. No.: 18/948,625

(22) Filed: Nov. 15, 2024

(65) Prior Publication Data

US 2025/0066814 A1 Feb. 27, 2025

Related U.S. Application Data

(63) Continuation of application No. PCT/CN2022/101539, filed on Jun. 27, 2022.

(30) Foreign Application Priority Data

May 16, 2022 (CN) .......................... 202210528997.2

(51) Int. Cl.
| | |
|---|---|
| *C12N 15/866* | (2006.01) |
| *C12N 5/07* | (2010.01) |
| *C12N 7/00* | (2006.01) |
| *C12N 15/86* | (2006.01) |
| *C12N 15/864* | (2006.01) |

(52) U.S. Cl.
CPC ........... *C12N 15/86* (2013.01); *C12N 5/0601* (2013.01); *C12N 7/00* (2013.01); *C12N 2710/14021* (2013.01); *C12N 2710/14043* (2013.01); *C12N 2710/14052* (2013.01); *C12N 2750/14143* (2013.01); *C12N 2750/14152* (2013.01)

(58) Field of Classification Search
None
See application file for complete search history.

(56) References Cited

U.S. PATENT DOCUMENTS

| | | |
|---|---|---|
| 2003/0148506 A1 | 8/2003 | Kotin et al. |
| 2004/0197895 A1 | 10/2004 | Kotin et al. |
| 2015/0240260 A1 | 8/2015 | Gomez Sebastain et al. |

FOREIGN PATENT DOCUMENTS

| | | |
|---|---|---|
| CN | 102007209 A | 4/2011 |
| CN | 106566829 A | 4/2017 |
| CN | 108699567 A | 10/2018 |
| CN | 112553257 A | 3/2021 |
| WO | 2017184879 A1 | 10/2017 |

OTHER PUBLICATIONS

Brown et al., COnserved Homolgous Regions between Two Baculovris DNAs, J gen Virology, 1987, pp. 207-212.*

Kikhno, Identification of a Conserved Non-Protein-Coding Genomic Element that Plays an Essential Role in Alphabaculovirus Pathogenesis, Plos One, 2015, pp. 1-15.*

Chen et al., The Transcriptome of the Baculovirus Autographa californica Multiple Nucleopolyhedrovirus in Trichoplusia ni Cells, JVI, 2013, pp. 6391-6405.*

Irina Kikhno, Identification of a conserved non-protein-coding genomic element that plays an essential role in Alphabaculovirus pathogenesis, PloS one, 2014, pp. 1-15, vol. 9, No. 4, e95322.

Zhihong Huang, et al., The Autographa californica Multiple Nucleopolyhedrovirus ac83 Gene Contains a cis-Acting Element That Is Essential for Nucleocapsid Assembly, J Virol, 2017, pp. 1-18, vol. 91, No. 5, e02110-16.

Benoît Doublet, et al., Antibiotic marker modifications of lambda Red and FLP helper plasmids, pKD46 and pCP20, for inactivation of chromosomal genes using PCR products in multidrug-resistant strains, Journal of Microbiological Methods, 2008, pp. 359-361, vol. 75.

Masashi Urabe, et al., Insect cells as a factory to produce adeno-associated virus type 2 vectors, Hum Gene Ther, 2002, pp. 1935-1943, vol. 13.

Dimitris Polychronopoulos, et al., Conserved non-coding elements: developmental gene regulation meets genome organization, Nucleic Acids Research, 2017, pp. 12611-12624, vol. 45, No. 22.

* cited by examiner

*Primary Examiner* — Maria Marvich
(74) *Attorney, Agent, or Firm* — Bayramoglu Law Offices LLC

(57) ABSTRACT

A baculovirus vector and a use thereof in the preparation of a recombinant adeno-associated virus (rAAV) in an insect cell are provided. The baculovirus vector includes an exogenous gene expression cassette and a stable sequence. The stable sequence is located at a site 5 kb or less from the exogenous gene expression cassette, and the stable sequence is a conserved noncoding element (CNE) sequence or a nucleocapsid assembly-essential element (NAE) sequence. When an insect cell is infected with a recombinant baculovirus (rBV) constructed in this way, after multiple continuous passages, production levels of the rBV and the rAAV still remain relatively stable.

17 Claims, 21 Drawing Sheets
Specification includes a Sequence Listing.

| | P3 | P4 | P5 | P6 | P7 | P8 | P9 | P10 |
|---|---|---|---|---|---|---|---|---|
| Bac-Tn7-ITR gp64 | 100% | 100% | 100% | 100% | 100% | 100% | 100% | 100% |
| Bac-Tn7-ITR tn7 | 92.46% | 32.23% | 17.52% | 20.58% | 8.56% | 6.78% | 4.23% | 2.45% |

SEQUENCE LISTING

```
Sequence total quantity: 17
SEQ ID NO: 1           moltype = DNA  length = 1590
FEATURE                Location/Qualifiers
misc_feature           1..1590
                       note = Expression cassette for homologous recombinant
source                 1..1590
                       mol_type = other DNA
                       organism = synthetic construct
SEQUENCE: 1
tgctcctgac gccgctcctg acggcgatgg ctgcgactgc ttgaagacgg ctggctgcga   60
ctgcttgaag acggctgggc ttcgggagat gttgtaaagt tgatgcggcg acggctgaga  120
gacagcctgt ggcggcggct gctgctggga gtggcggcgt tgatttggcg actcatggct  180
gggctggtag gatactgttc actaggctgt gaggcttgaa ctgtgcttac gagtagaacg  240
gcagctgtat ttatactgtt tatcagtact gcacgactga taagacaata gtggtggggg  300
aacttgccag gcaaaaatga gaagttccta tactttctag agaataggaa cttcatttaa  360
atggcgcgcc ttacgccccg ccctgccact catcgcagta ctgttgtatt cattaagcat  420
ctgccgacat ggaagccatc acaaacggca tgatgaacct gaatcgccag cggcatcagc  480
accttgtcgc cttgcgtata atatttgccc atggtgaaaa cggggggcgaa gaagttgtcc  540
atattggcca cgtttaaatc aaaactggtg aaactcaccc agggattggc tgagacgaaa  600
aacatattct caataaaccc tttagggaaa taggccaggt tttcaccgta acacgccaca  660
tcttgcgaat atatgtgtag aaactgccgg aaatcgtcgt ggtattcact ccagagcgat  720
gaaaacgttt cagtttgctc atggaaaacg gtgtaacaag ggtgaacact atcccatatc  780
accagctcac cgtctttcat tgccatacgt aattccggat gagcattcat caggcgggca  840
agaatgtgaa taaaggccgg ataaaacttg tgcttatttt tctttacggt ctttaaaaag  900
gccgtaatat ccagctgaac ggtctggtta taggtacatt gagcaactga ctgaaatgcc  960
tcaaatgtt cttacgatg ccattgggat atatcaacg tggtatatcc agtgattttt  1020
ttctccattt tagcttcctt agctcctgaa aatctcgaca actcaaaaaa tacgcccggt  1080
agtgatctta tttcattatg gtgaaagttg gaacctctta cgtgccgatc aacgtctcat  1140
tttcgccaaa agttggccca gggcttcccg gtatcaacag ggacaccagg atttatttat  1200
tctgcgaagt gatcttccgt cacaggtagg cgcgccgaag ttcctatact ttctagaaa   1260
taggaacttc tcattttaaa tttatcatat cacaggctgc agtttctgtt atctgtcccc  1320
cactcaggcg tgcagctata aaagcaggca ctcaccaact cgtaagcaca gttcgttgtg  1380
aagtgaacac ggagagcctg ccaataagca aaatgccaag ggacaccaac aatcgccacc  1440
ggtctacgcc atatgaacgt cctacgcttg aagatctccg cagacagttg caagacaatt  1500
tggacagcat aaaccgccga gacagaatgc aagaagaaca agaagaaac ctgcgctatc  1560
aagtgcgtag aaggcagcgt caaaaccagc                                  1590

SEQ ID NO: 2           moltype = DNA  length = 1277
FEATURE                Location/Qualifiers
misc_feature           1..1277
                       note = Expression cassette homologous recombinant
source                 1..1277
```

-continued

```
                          mol_type = other DNA
                          organism = synthetic construct
SEQUENCE: 2
cacccgacgt aataggctac gtgtcggata ttatgcaaaa cacttatatt gtaacgtggt    60
tcaacaccgt cgacctttcc acctatcacg aaagcgtgca tgatgaccgg attgaaattt   120
ttgatttctt aaatcaaaaa tttcaacctg ttgatcgaat cgtacacgat cgcgttagag   180
caaatgatga aaatcccaac gaagttccta tactttctag agaataggaa cttcatttaa   240
atggcgcgcc ttacgccccg ccctgccact catcgcagta ctgttgtatt cattaagcat   300
ctgccgacat ggaagccatc acaaacggca tgatgaacct gaatcgccag cggcatcagc   360
accttgtcgc cttgcgtata atatttgccc atggtgaaaa cgggggcgaa gaagttgtcc   420
atattggcca cgtttaaatc aaaactggtg aaactcaccc agggattggc tgagacgaaa   480
aacatattct caataaaccc tttagggaaa taggccaggt tttcaccgta acacgccaca   540
tcttgcgaat atatgtgtag aaactgccgg aaatcgtcgt ggtattcact ccagagcgat   600
gaaaacgttt cagtttgctc atggaaaacg gtgtaacaag ggtgaacact atcccatatc   660
accagctcac cgtctttcat tgccatacgt aattccggat gagcattcat caggcgggca   720
agaatgtgaa taaaggccgg ataaaacttg tgcttatttt tctttacggt ctttaaaaag   780
gccgtaatat ccagctgaac ggtctggtta taggtacatt gagcaactga ctgaaatgcc   840
tcaaaatgtt ctttacgatg ccattgggat atatcaacgg tggtatatcc agtgattttt   900
ttctccattt tagcttcctt agctcctgaa aatctcgaca actcaaaaaa tacgcccggt   960
agtgatctta tttcattatg gtgaaagttg gaacctctta cgtgccgatc aacgtctcat  1020
tttcgccaaa agttggccca gggcttcccg gtatcaacag ggacaccagg atttatttat  1080
tctgcgaagt gatcttccgt cacaggtagg cgcgccgaag ttcctatact ttctagagaa  1140
taggaacttc gcacgtcaaa aacggccaat acatggcgtg tcccgaagaa ttgtacgata  1200
acaacgaatt taaatgtaac atagaatcgg ataaattata ctatttggat aatttacaag  1260
aagattccat tgtatataa                                               1277

SEQ ID NO: 3            moltype = DNA   length = 2211
FEATURE                 Location/Qualifiers
misc_feature            1..2211
                        note = Cap gene
source                  1..2211
                        mol_type = other DNA
                        organism = synthetic construct
SEQUENCE: 3
ctggctgccg acggttatct acccgattgg ctcgaggaca accttagtga aggaattcgc    60
gagtggtggg ctttgaaacc tggagcccct caacccaagg caaatcaaca acatcaagac   120
aacgctcgag gtcttgtgct tccgggttac aaataccttg acccggcaa cggactcgac   180
aaggggggagc cggtcaacgc agcagacgcg gcggccctcg agcacgacaa ggcctacgac   240
cagcagctca aggccggaga caacccgtac ctcaagtaca accacgccga cgccgagttc   300
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcggggtg cacagcccgc taaaaagaga ctcaatttcg gtcagactgg cgacactgag   540
tcagtcccag accctcaacc aatcggagaa cctcccgcag ccccctcagg tgtgggatct   600
cttacaatgg cttcaggtgg tggcgcacca gtggcagaca ataacgaagg tgccgatgga   660
gtgggtagtt cctcgggaaa ttggcattgc gattcccaat ggctggggga cagagtcatc   720
accaccagca cccgaacctg ggccctgccc acctacaaca tcacctcta caagcaaatc   780
tccaacagca catctggagg atcttcaaat gacaacgcct acttcggcta cagcaccccc   840
tggggggtatt ttgacttcaa cagattccac tgccacttct caccacgtga ctggcagcga   900
ctcatcaaca caactggggg attccggcct aagcgactca acttcaagct cttcaacatt   960
caggtcaaag aggttacgga caacaatgga gtcaagacta ttgccaataa ccttaccagc  1020
acggtccagg tcttcacgga ctcagactat cagctcccgt acgtgctcgg gtcggctcac  1080
gagggctgcc tcccgccgtt cccagcggac gtttttcatga ttcctcagta cgggtatctg  1140
acgcttaatg atggaagcca ggcgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caaagaagga gaggaccgtt tctttccttt gtctggatct  1620
ttaattttttg gcaaacaagg aactggaaga gacaacgtgg atgcggacaa agtcatgata  1680
accaacgaag aagaaattaa aactactaac ccggtagcaa cggagtccta tggacaagtg  1740
gccacaaacc accagagtgc ccaagcacag cgcgaaccg gctgggttca aaaccaagga  1800
atacttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcacccgc tcctcagat cctcatcaaa aacacacctg tacctgcgga tcctccaacg  1980
gccttcaaca aggacaagct gaactctttc atcacccagt attctactgg ccaagtcagc  2040
gtgggatcg agtgggagct gcagaaggaa aacagcaagc gctggaaccc ggagatccag  2100
tacacttcca actattacaa gtctaataat gttgaatttg ctgttaatac tgaaggtgta  2160
tatagtgaac cccgccccat tggcaccaga tacctgactc gtaatctgta a           2211

SEQ ID NO: 4            moltype = DNA   length = 1866
FEATURE                 Location/Qualifiers
misc_feature            1..1866
                        note = Rep gene
source                  1..1866
                        mol_type = other DNA
                        organism = synthetic construct
```

```
SEQUENCE: 4
ctggcggggt tttacgagat tgtgattaag gtccccagcg accttgacgg gcatctgccc    60
ggcatttctg acagctttgt gaactgggtg gccgagaagg agtgggagtt gccgccagat   120
tctgacttgg atctgaatct gattgagcag gcacccctga ccgtggccga gaagctgcag   180
cgcgactttc tgacggagtg gcgccgtgtg agtaaggccc cggaggccct tttctttgtg   240
caatttgaga agggagagag ctacttccac ttacacgtgc tcgtggaaac caccgggtg   300
aaatccttag ttttgggacg tttcctgagt cagattcgcg aaaaactgat tcagagaatt   360
taccgcggga tcgagccgac tttgccaaac tggttcgcgg tcacaaagac cagaaacggc   420
gccggaggcg ggaacaaggt ggtggacgag tgctacatcc ccaattactt gctccccaaa   480
acccagcctg agctccagtg ggcgtggact aatttagaac agtatttaag cgcctgtttg   540
aatctcacgg agcgtaaacg gttggtggcg cagcatctga cgcacgtgtc gcagacgcag   600
gagcagaaca aagagaatca gaatcccaat tctgacgcgc cggtgatcag atcaaaaact   660
tcagccaggt acatggagct ggtcgggtgg ctcgtggaca aggggattac ctcggagaag   720
cagtggatcc aggaggacca ggcctcatac atctccttca atgcggcctc caactcgcag   780
tcccaaatca aggctgcctt ggacaatgcg ggaaagatta tgagcctgac taaaaccgcc   840
cccgactacc tggtgggcca gcagcccgtg gaggacattt ccagcaatcg gatttataaa   900
attttggaac taaacgggta cgatcccaa tatgcggctt ccgtcttct gggatgggc    960
acgaaaaagt tcggcaagag gaacaccatc tggctgtttg ggctgcaac taccgggaag  1020
accaacatcg cggaggccat agcccacact gtgcccttct acgggtgcgt aaactgacc  1080
aatgagaact ttcccttcaa cgactgtgtc gacaagatgg tgatctggtg ggaggagggg  1140
aagatgaccg ccaaggtcgt ggagtcggcc aaagccattc tcggaggaag caaggtgcgc  1200
gtggaccaga aatgcaagtc ctcggcccag atagacccga ctccgtgat cgtcacctcc  1260
aacaccaaca tgtgcgccgt gattgacggg aactcaacga ccttcgaaca ccagcagccg  1320
ttgcaagacc ggatgttcaa atttgaactc acccgccgtc tggatcatga ctttgggaag  1380
gtcaccaagc aggaagtcaa agactttttc cggtgggcaa aggatcacgt ggttgaggtg  1440
gagcatgaat tctacgtcaa aaagggtgga gccaagaaac gacccgcccc cagtgacgca  1500
gatataagtg agcccaaacg ggtgcgcgag tcagttgcgc agccatcgac gtcagacgcg  1560
gaagcttcga tcaactacgc agacaggtac caaaacaaat gttctcgtca cgtgggcatg  1620
aatctgatgc tgtttccctg cagacaatgc gagagaatga atcagaattc aaatatctgc  1680
ttcactcacg gacagaaaga ctgtttagag tgctttcccg tgtcagaatc tcaacccgtt  1740
tctgtcgtca aaaaggcgta tcagaaactg tgctacattc atcatatcat gggaaaggtg  1800
ccagacgctt gcactgcctg cgatctggtc aatgtggatt tggatgactg catctttgaa  1860
caataa                                                            1866

SEQ ID NO: 5          moltype = DNA   length = 156
FEATURE               Location/Qualifiers
misc_feature          1..156
                      note = CNE
source                1..156
                      mol_type = other DNA
                      organism = synthetic construct
SEQUENCE: 5
acttttttgt aatgcaaaaa agttgatagt gtagtagtat attgggagcg tatcgtacag    60
tgtagactat tctaataaaa tagtctacga tttgtagaga ttgtactgta tatggagtgt   120
caggcaaaag tgaacttttt tgcattgcaa aaaaat                             156

SEQ ID NO: 6          moltype = DNA   length = 2407
FEATURE               Location/Qualifiers
misc_feature          1..2407
                      note = ITR-GOI
source                1..2407
                      mol_type = other DNA
                      organism = synthetic construct
SEQUENCE: 6
cctgcaggca gctgcgcgct cgctcgctca ctgaggccgc ccgggcaaag cccgggcgtc    60
gggcgacctt tggtcgcccg gcctcagtga gcgagcgagc gcgcagagag ggagtggcca   120
actccatcac taggggttcc tgcggccgca cgcgccgccc gtcagtgggc agagcgcaca   180
tcgcccacag tccccgagaa gttggggga ggggtcggca attgaaccgg tgcctagaga   240
aggtggcgcg gggtaaactg ggaaagtgat gtcgtgtact ggctccgcct ttttcccgag   300
ggtgggggag aaccgtatat aagtgcagta gtcgccgtga acgttctttt tcgcaacggg   360
tttgccgcca gaacacgcgt aagggatccg ccaccatggt gagcaagggc gaggaggata   420
acatggccat catcaaggag ttcatgcgct tcaaggtgca catggagggc tccgtgaacg   480
gccacgagtt cgagatcgag ggcgagggcg agggccgccc ctacgagggc acccagaccg   540
ccaagctgaa ggtgaccaag ggtggccccg tgcccttcgc ctgggacatc ctgtcccctc   600
agttcatgta cggctccaag gcctacgtga gcaccccgc gacatcccc gactacttga   660
agctgtcctt ccccgagggc ttcaagtggg agcgcgtgat gaacttcgag gacggcggcg   720
tggtgaccgt gacccaggac tcctccctgc aggacgcgca gttcatctac aaggtgaagc   780
tgcgcggcac caacttcccc tccgacggcc ccgtaatgca gaagaagacc atgggctggg   840
aggcctcctc cgagcggatg taccccgagg acggcgcgt gaagcagag atcaagcaga   900
ggctgaagct gaaggacggc ggccactacg acgctgaggt caagaccacc tacaaggcca   960
agaagcccgt gcagctgccc ggcgcctaca acgtcaacat caagttggac atcacctccc  1020
acaacgagga ctacaccatc gtggaacagt acgaacgcgc cgagggccgc cactccaccg  1080
gcggcatgga cgagctgtac aagtaagaat tcgatatcaa gcttatcgat aatcaacctc  1140
tggattacaa aatttgtgaa agattgactg gtattcttaa ctatgttgct ccttttacgc  1200
tatgtggata cgctgcttta atgcctttgt atcatgctat tgcttccgt atggctttca  1260
ttttctcctc cttgtataaa tcctggttgc tgtctcttta tgaggagttg tggcccgttg  1320
tcaggcaacg tggcgtggtg tgcactgtgt ttgctgacgc aacccccact ggttggggca  1380
ttgccaccac ctgtcagctc ctttccggga ctttcgcttt ccccctccct attgccacgg  1440
cggaactcat cgccgcctgc cttgcccgct gctggacagg ggctcggctg ttgggcactg  1500
```

```
acaattccgt ggtgttgtcg gggaaatcat cgtcctttcc ttggctgctc gcctgtgttg   1560
ccacctggat tctgcgcggg acgtccttcc gctacgtccc ttcggccctc aatccagcgg   1620
accttccttc ccgcggcctg ctgccggctc tgcggcctct tccgcgtctt cgccttcgcc   1680
ctcagacgag tcggatctcc ctttgggccg cctccccgca tcgataccga gcgctgctcg   1740
agagatctac gggtggcatc cctgtgaccc ctcccagtg cctctcctgg ccctggaagt    1800
tgccactcca gtgcccacca gccttgtcct aataaaatta agttgcatca ttttgtctga   1860
ctaggtgtcc ttctataata ttatggggtg gaggggggtg gtatggagca aggggcaagt   1920
tgggaagaca acctgtaggg cctgcggggt ctattgggaa ccaagctgga gtgcagtggc   1980
acaatcttgg ctcactgcaa tctccgcctc ctgggttcaa gcgattctcc tgcctcagcc   2040
tcccgagttg ttgggattcc aggcatgcat gaccaggctc agctaatttt tgtttttttg   2100
gtagagacgg ggtttcacca tattggccag gctggtctcc aactcctaat ctcaggtgat   2160
ctacccacct tggcctccca aattgctggg attacaggcg tgaaccactg ctcccttccc   2220
tgtccttctg attttgtagg taaccacgtg cggaccgagc ggccgcagga acccctagtg   2280
atggagttgg ccactccctc tctgcgcgct cgctcgctca ctgaggccgg gcgaccaaag   2340
gtcgcccgac gcccgggctt tgcccgggcg gcctcagtga gcgagcgagc gcgcagctgc   2400
ctgcagg                                                             2407

SEQ ID NO: 7               moltype = DNA   length = 200
FEATURE                    Location/Qualifiers
misc_feature               1..200
                           note = NAE
source                     1..200
                           mol_type = other DNA
                           organism = synthetic construct
SEQUENCE: 7
cattttcagc gacgtatatt gacaaatata ctacagtcgg acgtttgtgc cgacctatat   60
actacacttt accaaaaata tactacacta aactctaaat atactacaac tccacttcaa   120
tataaccaca ctctcgtaaa acggcccaaa aatatcgaaa tatatggggc aaatacacgt   180
ttaaaaaacg ctacgattcc                                               200

SEQ ID NO: 8               moltype = DNA   length = 20
FEATURE                    Location/Qualifiers
source                     1..20
                           mol_type = other DNA
                           organism = synthetic construct
SEQUENCE: 8
aacttggaca ttaccccgcc                                               20

SEQ ID NO: 9               moltype = DNA   length = 20
FEATURE                    Location/Qualifiers
source                     1..20
                           mol_type = other DNA
                           organism = synthetic construct
SEQUENCE: 9
ccgttgtacg catacgcctg                                               20

SEQ ID NO: 10              moltype = DNA   length = 20
FEATURE                    Location/Qualifiers
source                     1..20
                           mol_type = other DNA
                           organism = synthetic construct
SEQUENCE: 10
gaacaaggtg gtggacgagt                                               20

SEQ ID NO: 11              moltype = DNA   length = 20
FEATURE                    Location/Qualifiers
source                     1..20
                           mol_type = other DNA
                           organism = synthetic construct
SEQUENCE: 11
attcaaacag gcgcttaaat                                               20

SEQ ID NO: 12              moltype = DNA   length = 23
FEATURE                    Location/Qualifiers
source                     1..23
                           mol_type = other DNA
                           organism = synthetic construct
SEQUENCE: 12
tcgtattagc ttacgacgct aca                                           23

SEQ ID NO: 13              moltype = DNA   length = 20
FEATURE                    Location/Qualifiers
source                     1..20
                           mol_type = other DNA
                           organism = synthetic construct
SEQUENCE: 13
tagttgggaa ctgggagggg                                               20

SEQ ID NO: 14              moltype = DNA   length = 21
```

-continued

```
FEATURE              Location/Qualifiers
source               1..21
                     mol_type = other DNA
                     organism = synthetic construct
SEQUENCE: 14
ggaaccccta gtgatggagt t                                          21

SEQ ID NO: 15        moltype = DNA   length = 16
FEATURE              Location/Qualifiers
source               1..16
                     mol_type = other DNA
                     organism = synthetic construct
SEQUENCE: 15
cggcctcagt gagcga                                                16

SEQ ID NO: 16        moltype = DNA   length = 18
FEATURE              Location/Qualifiers
source               1..18
                     mol_type = other DNA
                     organism = synthetic construct
SEQUENCE: 16
ccgttgtcag gcaacgtg                                              18

SEQ ID NO: 17        moltype = DNA   length = 20
FEATURE              Location/Qualifiers
source               1..20
                     mol_type = other DNA
                     organism = synthetic construct
SEQUENCE: 17
agctgacagg tggtggcaat                                            20
```

BACULOVIRUS VECTOR AND USE THEREOF IN PREPARATION OF RECOMBINANT ADENO-ASSOCIATED VIRUS (rAAV) IN INSECT CELL

CROSS REFERENCE TO THE RELATED APPLICATIONS

This application is a continuation application of International Application No. PCT/CN2022/101539, filed on Jun. 27, 2022, which is based upon and claims priority to Chinese Patent Application No. 202210528997.2, filed on May 16, 2022, the entire contents of which are incorporated herein by reference.

SEQUENCE LISTING

The instant application contains a Sequence Listing which has been submitted in XML format via EFS-Web and is hereby incorporated by reference in its entirety. Said XML copy is named GBWHHZY011_Sequence_Listing.xmlt, created on 11/13/2024, and is 28,220 bytes in size.

TECHNICAL FIELD

The present disclosure belongs to the technical field of genetic engineering, and specifically, relates to a baculovirus vector and a use thereof in preparation of a recombinant adeno-associated virus (rAAV) in an insect cell.

BACKGROUND

Recombinant adeno-associated virus (rAAV) is currently one of the most promising vectors in the field of gene therapy. At present, there are mainly the following two rAAV production systems: 1. the conventional production system adopting mammalian cells (such as 293 cells, COS cells, HeLa cells, and KB cells) and 2. the production system adopting insect cells. In mammalian cell-based production systems, a single cell has a low yield of rAAV particles, and there is a high risk of contamination during cultivation, which limits the large-scale production of rAAV in mammalian cells and the application of rAAV.

In order to overcome the above problems, the production system for preparing rAAV with baculovirus-infected insect cells has been developed. That is, the rep gene, the cap gene, and the inverted terminal repeat (ITR) core expression element that provide AAV are integrated into three different baculovirus genomes through Tn7 transposons, respectively, and then insect cells are co-infected with three recombinant baculoviruses (rBVs) produced accordingly to prepare rAAV (Urabe et al., 2002, Hum. Gene Ther. 13: 1935-1943; US20030148506; and US20040197895).

However, due to the shortcomings of the rBVs themselves, such as easy loss of exogenous genes during continuous passages, the rBVs carrying adeno-associated virus (AAV) genomes will become unstable after multiple passages, resulting in the decrease of an rAAV yield. The existing rBV vectors are not suitable for the large-scale rAAV production and application with high stability requirements. Therefore, when used in the production of drug vectors for gene therapy, the existing rBV vectors still have room for improvement.

SUMMARY

In view of the defects of the prior art, an objective of the present disclosure is to provide a baculovirus vector and a use thereof in preparation of rAAV in an insect cell. The present disclosure is intended to solve the problem that rBV will become unstable after passages when used in preparation of rAAV.

In order to achieve the above objective, the present disclosure provides a baculovirus vector, including an exogenous gene expression cassette and a stable sequence, where the stable sequence is located at a site 5 kb or less from the exogenous gene expression cassette, and the stable sequence is a conserved noncoding element (CNE) sequence or a nucleocapsid assembly-essential element (NAE) sequence.

Preferably, the exogenous gene expression cassette is at least one of a cap gene expression cassette of AAV, a rep gene expression cassette of AAV, and an AAV ITR core expression element carrying a heterologous functional gene; and the stable sequence is located at a site 5 kb or less from at least one of start and stop ends of the cap gene expression cassette, start and stop ends of the rep gene expression cassette, and two ends of the AAV ITR core expression element carrying the heterologous functional gene.

Preferably, the exogenous gene expression cassette is the cap gene expression cassette and the rep gene expression cassette.

Preferably, the baculovirus vector includes the cap gene expression cassette, the stable sequence, and the rep gene expression cassette sequentially from 5' to 3'.

Preferably, the baculovirus vector includes the rep gene expression cassette, the stable sequence, and the cap gene expression cassette sequentially from 5' to 3'.

Preferably, the stable sequence is located between the cap gene expression cassette and the rep gene expression cassette, and two ends of the stable sequence are close to a start end of the cap gene expression cassette and a start end of the rep gene expression cassette, respectively.

Preferably, the exogenous gene expression cassette is the AAV ITR core expression element carrying the heterologous functional gene.

Preferably, the exogenous gene expression cassette is the AAV ITR core expression element carrying the heterologous functional gene and the cap gene expression cassette.

Preferably, the exogenous gene expression cassette is a rep78 gene expression cassette of AAV, the baculovirus vector further includes a rep52 gene expression cassette of AAV, and the stable sequence is located between the rep78 gene expression cassette and the rep52 gene expression cassette.

Preferably, the exogenous gene expression cassette is a rep52 gene expression cassette of AAV, the baculovirus vector further includes a rep78 gene expression cassette of AAV, and the stable sequence is located between the rep52 gene expression cassette and the rep78 gene expression cassette.

Preferably, two ends of the stable sequence are close to a start end of the rep78 gene expression cassette and a start end of the rep52 gene expression cassette, respectively.

Preferably, a promoter to initiate expression of the rep78 gene expression cassette is a baculovirus early promoter, and a promoter to initiate expression of the rep52 gene expression cassette is a baculovirus very late promoter.

Preferably, the baculovirus early promoter is a ΔIE1 promoter, and the baculovirus very late promoter is a p10 promoter.

Preferably, the exogenous gene expression cassette is used to express a reporter protein or a therapeutic gene product.

Preferably, the baculovirus vector is an rBV transfer vector, and the exogenous gene expression cassette and the stable sequence are located between terminal elements Tn7L and Tn7R of a transposon Tn7 of the rBV transfer vector.

Preferably, the baculovirus vector is an rBV shuttle vector.

Preferably, the rBV shuttle vector is obtained by inserting the exogenous gene expression cassette and the stable sequence into a first baculovirus shuttle vector at a transposon insertion site through first rBV transfer vector-mediated Tn7 transposition, and the CNE sequence or the NAE sequence is deleted in a baculovirus genome of the first baculovirus shuttle vector.

Preferably, the rBV shuttle vector is obtained by inserting the exogenous gene expression cassette into a second baculovirus shuttle vector at a site near the CNE sequence or the NAE sequence in the second baculovirus shuttle vector through transfer vector-mediated Red homologous recombination.

According to another aspect of the present disclosure, a use of any one of the above-described baculovirus vectors in preparation of rBV and/or rAAV in an insect cell is provided.

According to another aspect of the present disclosure, an insect cell including any one of the above-described baculovirus vectors is provided.

Preferably, the baculovirus vector is any one of the above-described rBV shuttle vectors.

Preferably, the insect cell further includes a second vector, where the second vector includes an AAV ITR core expression element with a heterologous functional gene, and the exogenous gene expression cassette is the cap gene expression cassette of AAV and the rep gene expression cassette of AAV.

According to another aspect of the present disclosure, a method for in vitro growth or production of rBV is provided, including: providing an insect cell culture including any one of the above-described insect cells, and cultivating the insect cell.

According to another aspect of the present disclosure, a method for in vitro growth or production of rAAV is provided, including: providing an insect cell culture including any one of the above-described insect cells, and cultivating the insect cell.

In general, compared with the prior art, the above technical solutions conceived by the present disclosure have the following beneficial effects:

In the present disclosure, a CNE or NAE sequence is constructed at a site near an exogenous gene expression cassette in an rBV vector, and thus a production level of the rBV can remain relatively stable during continuous passages. In addition, a CNE or NAE sequence is constructed at a site near a functional protein expression cassette or an ITR core expression element necessary for the production of rAAV, and thus when an insect cell is infected with the recombinant bacmid, production levels of the rBV and the rAAV are relatively stable during continuous passages. During passages of the rBV, if the cap and rep gene expression cassettes are lost, a defective bacmid genome with the expression cassettes lost cannot be replicated or packaged into a capsid, which ensures the stability of the rBV carrying the CNE (or NAE) sequence and the cap and rep gene expression cassettes during passages. As a result, an insect cell including the baculovirus vector can stably maintain the production of high-titer rAAV even after continuous passages.

DETAILED DESCRIPTION OF THE EMBODIMENTS

Figures 1, 2:
FIG. 1 is a schematic diagram of a first homologous recombination expression cassette of a targeting CNE sequence constructed in Example 1 of the present disclosure.
FIG. 2 is a schematic diagram of a second homologous recombination expression cassette of a targeting NAE sequence constructed in Example 1 of the present disclosure.

In order to make the objectives, technical solutions, and advantages of the present disclosure clear, the present disclosure is further described in detail below with reference to the accompanying drawings and embodiments. It should be understood that the specific embodiments described herein are merely intended to explain the present disclosure, rather than to limit the present disclosure.

Unless otherwise defined, all technical and scientific terms used herein have the same meaning as commonly understood by those skilled in the technical field of the present disclosure. The terms used in the specification of the present disclosure herein are merely for the purpose of describing specific embodiments, and are not intended to limit the present disclosure. The term "and/or" used herein includes any and all combinations of one or more of the associated listed items.

In addition, the terms such as "first" and "second" are used only for the purpose of description and should not be construed as indicating or implying the relative importance, or implicitly indicating the quantity of indicated technical features. Therefore, features defined by "first" and "second" may explicitly or implicitly include at least one of the features. In the descriptions about the present disclosure, "a plurality of" means at least two, such as two or three, unless otherwise clearly and specifically limited. In the description of the present disclosure, "several" means at least one, such as one or two, unless otherwise clearly and specifically defined.

As used herein, an expression cassette refers to a nucleic acid construct carrying a coding sequence and a regulatory sequence that can be operably linked when introduced into a host cell, where the coding sequence and the regulatory sequence lead to the transcription and/or translation of RNA or a polypeptide. It should be understood that the expression cassette includes a promoter allowing the initiation of transcription, an open reading frame of a target gene, and a transcription terminator. Generally, a promoter sequence is located upstream of a target gene, and a distance between the promoter sequence and the target gene is compatible with the expression control.

Cis-acting elements refer to specific DNA sequences linked to structural genes in series, and are binding sites for transcription factors. The cis-acting elements can regulate the accurate initiation of gene transcription and the transcription efficiency by binding to transcription factors. The cis-acting elements include promoters, enhancers, regulatory sequences, inducible elements, etc. The cis-acting elements can participate in the regulation of gene expression, but do not code any protein themselves and merely provide one action site.

AAV is a single-stranded DNA virus that has a simple genome structure with an overall length of about 4.7 kb. A genome of AAV includes a rep gene expression cassette, a cap gene expression cassette, and an AAV inverted terminal repeat (ITR) at two ends of the genome, which are the three elements necessary to package AAV A Cap gene encodes a structural VP capsid protein including three overlapping open reading frames that encode the three subunits of VP1, VP2, and VP3, respectively. A Rep gene encodes the four overlapping multifunctional proteins of Rep78, Rep68, Rep52, and Rep40, which are involved in the replication and integration of AAV. ITR is a palindromic structure of 125 nucleotides at two ends of a genome. ITR can form a self-complementary inverted T-shaped hairpin structure. ITR is a cis-acting element required for the initiation of DNA replication and the package of a recombinant AAV genome to generate infectious virions. As a defective virus, AAV cannot replicate independently in the absence of a helper virus. Therefore, AAV can only be integrated into a chromosome of a host cell in a targeted manner, and is in a latent state. In the presence of a helper virus, the increased expression of the rep gene can rescue an AAV genome integrated in a chromosome of a host cell for mass replication to produce AAV DNA, and a single-stranded rAAV genome can be packaged into infectious virions under an action of a VP capsid protein.

It has been found that conserved non-protein-coding elements (CNEs) are present in all sequenced genomes of alphabaculoviruses, and have a highly-homologous sequence of 154 bp to 157 bp. It has been reported that an at-rich CNE sequence located in an ac152 region of a genome of an *Autographa californica* multiple nucleopolyhedro-virus (AcMNPV) may be a cis-acting element essential for virion production.

NAE sequences have been first discovered as essential elements for nucleocapsid assembly in alphabaculoviruses. NAE sequences play an essential role in the nucleocapsid assembly. The natural NAE sequences are mapped to an ac83 gene and homologous genes thereof in alphabaculoviruses, and are located at the proximal end (CN106566829A). ac83 is a core gene associated with the baculovirus nucleocapsid assembly. ac83 has an overall length of 2,544 bp and a predicted molecular weight of 96.2 kDa, and can encode 847 amino acids. The knockout of ac83 does not affect the replication of a virus genome, but can completely block the virus nucleocapsid assembly, and accordingly, a large number of hollow capsid precursors can be observed in nuclei under an electron microscope.

Positions of the natural CNE and NAE sequences in baculovirus genomes are conserved to some extent. There is currently no literature reporting that these two sequences can be used in baculovirus systems to improve the stability of AAV production, which is verified by the present disclosure.

The present disclosure provides a baculovirus vector, including an exogenous gene expression cassette and a stable sequence. The stable sequence is located at a site 5 kb or less from the exogenous gene expression cassette, and the stable sequence is a CNE sequence or an NAE sequence.

The exogenous gene expression cassette involved in the present disclosure may be either an element essential for producing rAAV or a coding sequence for expressing a foreign protein. For example, the foreign protein includes, but is not limited to, a reporter protein or a therapeutic gene product. When the exogenous gene expression cassette is the element essential for producing rAAV, the exogenous gene expression cassette can specifically be at least one of a cap gene expression cassette of AAV, a rep gene expression cassette of AAV, and an AAV ITR core expression element carrying a heterologous functional gene, and the stable sequence is located at a site 5 kb or less from at least one of start and stop ends of the cap gene expression cassette, start and stop ends of the rep gene expression cassette, and two ends of the AAV ITR core expression element carrying the heterologous functional gene.

The AAV ITR core expression element carrying the heterologous functional gene is the heterologous functional gene and an AAV ITR located at two ends of the heterologous functional gene. The heterologous functional gene may be at least one nucleotide sequence encoding a gene of interest (GOI). The GOI may be a therapeutic gene product. Specifically, the GOI can be a polypeptide, an RNA molecule (siRNA), or another gene product, for example, including, but not limited to, a lipoprotein lipase, an apolipoprotein, a cytokine, an interleukin, or an interferon. The GOI can also be a reporter protein for assessing the transformation and expression of a vector, for example, including, but not limited to, a fluorescent protein (green fluorescent protein (GFP) and red fluorescent protein (RFP)), a chloramphenicol acetyltransferase, β-galactosidase, β-glucuronidase, renilla luciferase, firefly luciferase, or alkaline phosphatase.

In the present disclosure, in order to improve the stability of AAV production of a baculovirus system in an insect cell, a stable sequence, namely, a CNE sequence or an NAE sequence, is constructed at a site near the three essential elements for the package of AAV. Specifically, a positional relationship between the stable sequence and the three elements can be presented in various forms: (1) The exogenous gene expression cassette is a cap gene expression cassette of AAV, and the stable sequence is located at a site 5 kb or less from a start end and/or a stop end of the cap gene expression cassette. (2) The exogenous gene expression cassette is a rep gene expression cassette of AAV, and the stable sequence is located at a site 5 kb or less from a start end and/or a stop end of the rep gene expression cassette. (3) The exogenous gene expression cassette is an AAV ITR core expression element carrying a heterologous functional gene (namely, ITR-GOI), and the stable sequence is located at a site 5 kb or less from one end and/or the other end of the ITR-GOI. (4) The exogenous gene expression cassette is a cap gene expression cassette of AAV and a rep gene expression cassette of AAV, and the stable sequence is located at a site 5 kb or less from at least one of start and stop ends of the cap gene expression cassette and start and stop ends of the rep gene expression cassette. (5) The exogenous gene expression cassette is a cap gene expression cassette of AAV and an AAV ITR core expression element carrying a heterologous functional gene, and the stable sequence is located at a site 5 kb or less from at least one of start and stop ends of the cap gene expression cassette and two ends of the ITR-GOI. (6) The exogenous gene expression cassette is a rep gene expression cassette of AAV and an AAV ITR core expression element carrying a heterologous functional gene, and the stable sequence is located at a site 5 kb or less from at least one of start and stop ends of the rep gene expression cassette and two ends of the ITR-GOI. (7) The exogenous gene expression cassette is a cap gene expression cassette of AAV, a rep gene expression cassette of AAV, and an AAV ITR core expression element carrying a heterologous functional gene, and the stable sequence is located at a site 5 kb or less from at least one of start and stop ends of the cap gene expression cassette, start and stop ends of the rep gene expression cassette, and two ends of the ITR-GOI.

As a preferred embodiment, the exogenous gene expression cassette is a cap gene expression cassette and a rep gene expression cassette of AAV, and the stable sequence is located at a site 5 kb or less from at least one of start and stop ends of the cap gene expression cassette and start and stop ends of the rep gene expression cassette.

It should be noted that the present disclosure does not limit the specific positions and directions of the cap gene expression cassette and the rep gene expression cassette. The cap gene expression cassette, the rep gene expression cassette, and the stable sequence can be arranged in the following six modes: 1. The cap gene expression cassette, the rep gene expression cassette, and the stable sequence are arranged sequentially from 5' terminus to 3' terminus. 2. The rep gene expression cassette, the cap gene expression cassette, and the stable sequence are arranged sequentially from 5' terminus to 3' terminus. 3. The cap gene expression cassette, the stable sequence, and the rep gene expression cassette are arranged sequentially from 5' terminus to 3' terminus. 4. The rep gene expression cassette, the stable sequence, and the cap gene expression cassette are arranged sequentially from 5' terminus to 3' terminus. 5. The stable sequence, the cap gene expression cassette, and the rep gene expression cassette are arranged sequentially from 5' terminus to 3' terminus. 6. The stable sequence, the rep gene expression cassette, and the cap gene expression cassette are arranged sequentially from 5' terminus to 3' terminus. The cap gene expression cassette and the rep gene expression cassette can be in a same direction or in opposite directions. The cap gene expression cassette can be arranged on the baculovirus vector in a sequence either from 5' terminus to 3' terminus or from 3' terminus to 5' terminus. Similarly, the rep gene expression cassette can be arranged on the baculovirus vector in a sequence either from 5' terminus to 3' terminus or from 3' terminus to 5' terminus.

In addition, a distance of the stable sequence from the cap gene expression cassette and/or the rep gene expression cassette can be about 0.5 kb, about 1 kb, about 1.5 kb, about 2 kb, about 2.5 kb, about 3 kb, about 3.5 kb, about 4 kb, about 4.5 kb, or about 5 kb. The distance of the stable sequence from the cap gene expression cassette and/or the rep gene expression cassette can be a distance of the stable sequence from a start end or a stop end of the gene. In some embodiments, the CNE sequence may be a CNE sequence identical to a CNE sequence of wild-type AcMNPV, or a CNE sequence derived from another baculovirus, or an artificial CNE sequence that has a sequence identity of at least 50%, at least 60%, at least 70%, at least 80%, at least 85%, at least 90%, at least 95%, or more with the CNE sequence of wild-type AcMNPV. Similarly, the NAE sequence may be an NAE sequence identical to an NAE sequence of wild-type AcMNPV, or an NAE sequence derived from another baculovirus, or an artificial NAE sequence that has a sequence identity of at least 50%, at least 60%, at least 70%, at least 80%, at least 85%, at least 90%, at least 95%, or more with the NAE sequence of wild-type AcMNPV As a preferred embodiment, the stable sequence is located between the cap gene expression cassette and the rep gene expression cassette. Specifically, the baculovirus vector includes the cap gene expression cassette, the CNE sequence, and the rep gene expression cassette sequentially from 5' to 3', or the baculovirus vector includes the cap gene expression cassette, the NAE sequence, and the rep gene expression cassette sequentially from 5' to 3', or the baculovirus vector includes the rep gene expression cassette, the CNE sequence, and the cap gene expression cassette sequentially from 5' to 3', or the baculovirus vector includes the rep gene expression cassette, the NAE sequence, and the cap gene expression cassette sequentially from 5' to 3'. Further preferably, two ends of the stable sequence are close to a start end of the cap gene expression cassette and a start end of the rep gene expression cassette, respectively. That is, the cap gene expression cassette and the rep gene expression cassette are in opposite directions, and starting ends of the cap gene expression cassette and the rep gene expression cassette are arranged oppositely and face towards the stable sequence.

As a preferred embodiment, a cap gene and a rep gene can be regulated by the baculovirus very late gene-expression strong promoters p10 and polh, respectively, or the cap gene is regulated by the polh promoter and the rep gene is regulated by the p10 promoter.

The rep gene expression cassette of the present disclosure at least encodes Rep78 and Rep52 proteins or Rep68 and Rep40 proteins. The rep gene expression cassette can include two overlapping open reading frames linked by a same regulatory sequence, and can include two expression cassettes, where the two expression cassettes have a respective regulatory sequence and express a protein. In some embodiments, the baculovirus vector may include the two independent gene expression cassettes of rep78 and rep52, and the expressions of the two gene expression cassettes are initiated by two promoters, respectively. For example, the stable sequence is located between the rep78 and rep52 gene expression cassettes. Preferably, two ends of the stable sequence are close to a start end of the rep78 gene expression cassette and a start end of the rep52 gene expression cassette, respectively. A promoter to initiate the expression of the rep78 gene expression cassette can be a baculovirus early promoter, such as a ΔIE1 promoter, and a promoter to initiate the expression of the rep52 gene expression cassette can be a baculovirus very late promoter, such as a p10 promoter or a polh promoter.

The baculovirus vector provided by the present disclosure can be a baculovirus, a baculovirus transfer vector, or a baculovirus shuttle vector (which is also known as a baculovirus plasmid and referred to as bacmid). The baculovirus transfer vector involved in the present disclosure usually includes a strong promoter and terminal elements Tn7L and Tn7R of a transposon Tn7, such as, but not limited to, a pFastBac vector. When a baculovirus vector including an exogenous gene expression cassette and a stable sequence is a first rBV transfer vector, the exogenous gene expression cassette and the stable sequence are located between terminal elements Tn7L and Tn7R of a transposon Tn7 of the first rBV transfer vector. The exogenous gene expression cassette and the stable sequence are together inserted into a first baculovirus shuttle vector at a transposon insertion site through first rBV transfer vector-mediated Tn7 transposition to obtain a first rBV shuttle vector carrying the exogenous gene expression cassette and the stable sequence. It should be noted that, when the stable sequence is a CNE sequence, the CNE sequence is deleted in a baculovirus genome carried by the corresponding first baculovirus shuttle vector, and when the stable sequence is an NAE sequence, the NAE sequence is deleted in a baculovirus genome carried by the corresponding first baculovirus shuttle vector. There is another method to prepare the rBV shuttle vector carrying the exogenous gene expression cassette and the stable sequence: a transfer vector with the exogenous gene expression cassette cloned and a second baculovirus shuttle vector carrying a complete baculovirus genome (including the normal CNE and NAE sequences) are subjected to Red homologous recombination, such that the exogenous gene expression cassette is inserted into the second baculovirus shuttle vector at a site near the CNE sequence or the NAE sequence to obtain a second rBV shuttle vector carrying the exogenous gene expression cassette and the stable sequence.

The baculovirus vector provided by the present disclosure can be used for preparing rBV and/or rAAV in an insect cell. Compared with insect cells carrying vectors without the CNE or NAE sequence, an insect cell carrying the baculovirus vector of the present disclosure can stably maintain the production of high-titer rAAV even after continuous passages.

The present disclosure also provides an insect cell carrying the above-described baculovirus vector, such as, but not limited to, a Sf9 cell from *Spodoptera frugiperda*, a Tni Pro cell from *Trichoplusia ni*, or an E4a cell from *Estima acrea* that carries the baculovirus vector, and preferably the Sf9 cell carrying the baculovirus vector.

The present disclosure also provides a method for in vitro growth or production of rBV, including: providing an insect cell culture including the above-described insect cell, and cultivating the insect cell. The insect cell is produced by infecting an insect cell with any one of the rBVs carrying the exogenous gene expression cassette and the stable sequence described above or by transfecting an insect cell with any one of the recombinant bacmids carrying the exogenous gene expression cassette and the stable sequence described above.

The present disclosure also provides a method for in vitro growth or production of rAAV, including: providing an insect cell culture including the insect cell described above, and cultivating the insect cell. The insect cell is produced by infecting an insect cell with one or more rBVs carrying the exogenous gene expression cassette and the stable sequence described above or by transfecting an insect cell with one or more recombinant bacmids carrying the exogenous gene expression cassette and the stable sequence described above. The CNE sequence or the NAE sequence is located at a site 5 kb or less from at least one of a start end of the cap gene expression cassette, a stop end of the cap gene expression cassette, a start end of the rep gene expression cassette, and a stop end of the rep gene expression cassette. The insect cell can be repeatedly passaged for multiple generations with little or no loss of AAV production, such as at least 3 generations, at least 4 generations, at least 5 generations, at least 6 generations, at least 7 generations, at least 8 generations, at least 9 generations, and at least 10 generations.

It should be noted that the insect cell for growth or production of rBV or rAAV can include: the following three bacmids: a recombinant bacmid carrying the cap gene expression cassette of AAV, a recombinant bacmid carrying the rep gene expression cassette of AAV, and a recombinant bacmid carrying the ITR-GOI; or the following two bacmids: a recombinant bacmid carrying both the cap and rep gene expression cassettes of AAV, and a recombinant bacmid carrying the ITR-GOI; or the following two bacmids: a recombinant bacmid carrying only the rep gene expression cassette of AAV, and a recombinant bacmid carrying both the cap gene expression cassette of AAV and the ITR-GOI; or the following one bacmid: a recombinant bacmid carrying the cap and rep gene expression cassettes of AAV and the ITR-GOI after integration. The stable sequence (the CNE or NAE sequence) is located near at least one of the cap gene expression cassette of AAV, the rep gene expression cassette of AAV, and the AAV ITR core expression element with the heterologous functional gene.

In an embodiment, rAAV is produced by a two-baculovirus system, and a main process is as follows: The rep and cap genes of AAV, in combination with the CNE sequence (or the NAE sequence) nearby, are integrated into a baculovirus genome through transfer vector-mediated Tn7 recombination, the ITR core expression element with the heterologous functional gene is integrated into another baculovirus genome through transfer vector-mediated Tn7 recombination, and then a host cell is co-infected with resulting two rBVs (BEVs) to produce the rAAV.

The above technical solutions will be described in detail below in conjunction with specific examples.

Example 1 Construction of a CNE Sequence-Deleted Bacmid ΔCNE-Bac and an NAE Sequence-Deleted Bacmid ΔNAE-Bac Red recombination is an efficient recombinant method at a bacterial level, and can be used in *Escherichia coli* (DH10Bac) to rapidly modify an rBV genome. The Red recombination refers to homologous recombination of a linear DNA fragment carrying a homologous arm introduced into a cell with a specific target sequence of a genome using a X bacteriophage Red recombinase (including the three proteins of Exo, Beta, and Gam) to allow the substitution of a target gene (Doublet et al., 2008, J Microbiol Methods, 75 (2): 359-361).

A first homologous recombination expression cassette (SEQ ID NO: 1) of a targeting CNE sequence was first constructed. As shown in FIG. 1, the first homologous recombination expression cassette included an upstream homologous sequence of CNE, a chloramphenicol (Chol) resistance gene expression cassette, and a downstream homologous sequence of CNE sequentially from 5' to 3'. Then, a CNE sequence on a bacmid was replaced with the first homologous recombination expression cassette by the Red recombination technique, so as to obtain the CNE sequence-deleted bacmid ΔCNE-Bac.

Similarly, a second homologous recombination expression cassette (SEQ ID NO: 2) of a targeting NAE sequence was first constructed. As shown in FIG. 2, the second homologous recombination expression cassette included an upstream homologous sequence of NAE, a Chol resistance gene expression cassette, and a downstream homologous sequence of NAE sequentially from 5' to 3'. Then, an NAE sequence on a bacmid was replaced with the second homologous recombination expression cassette by the Red recombination technique, so as to obtain the NAE sequence-deleted bacmid ΔNAE-Bac.

Figure 3:
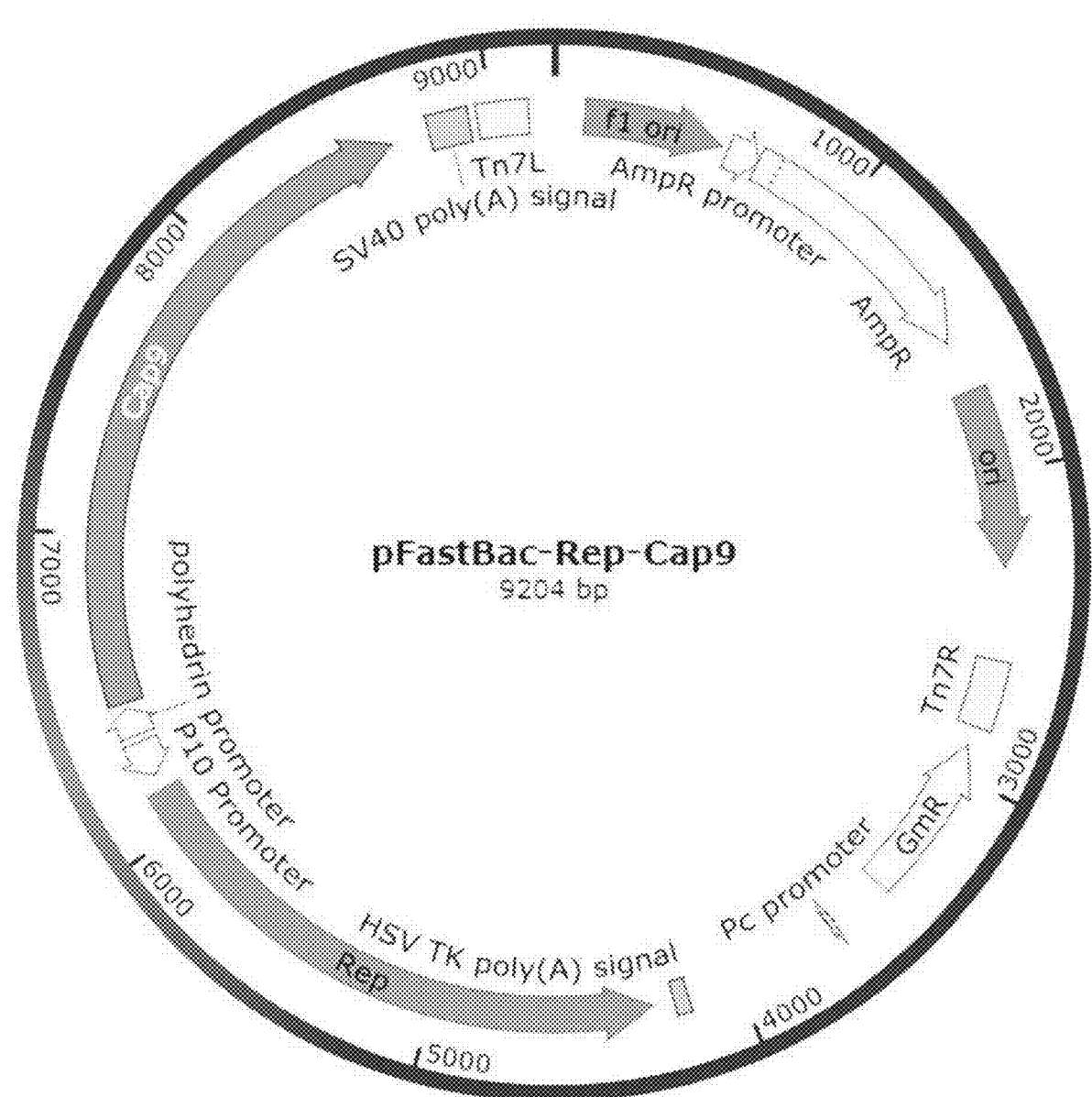
FIG. 3 is a schematic diagram of an rBV transfer vector pFastBac-Rep-Cap9 constructed in Example 2 of the present disclosure.

Example 2 Construction of Recombinant Transfer Vectors pFastBac-Rep-Cap9, pFastBac-Rep-CNE-Cap9, pFastBac-ITR, and pFastBac-ITR-CNE that Include or do not Include a CNE Sequence A recombinant transfer vector carrying Cap and Rep expression cassettes of AAV was constructed. A Cap gene sequence of AAV9 and a Rep gene sequence of AAV2 were first amplified from an AAV genome through polymerase chain reaction (PCR), and then the Cap gene sequence (SEQ ID NO: 3) and the Rep gene sequence (SEQ ID NO: 4) were inserted into a pFastBac vector through enzyme digestion and enzyme ligation to obtain a recombinant transfer vector pFastBac-Rep-Cap9, as shown in FIG. 3.

Figure 4:
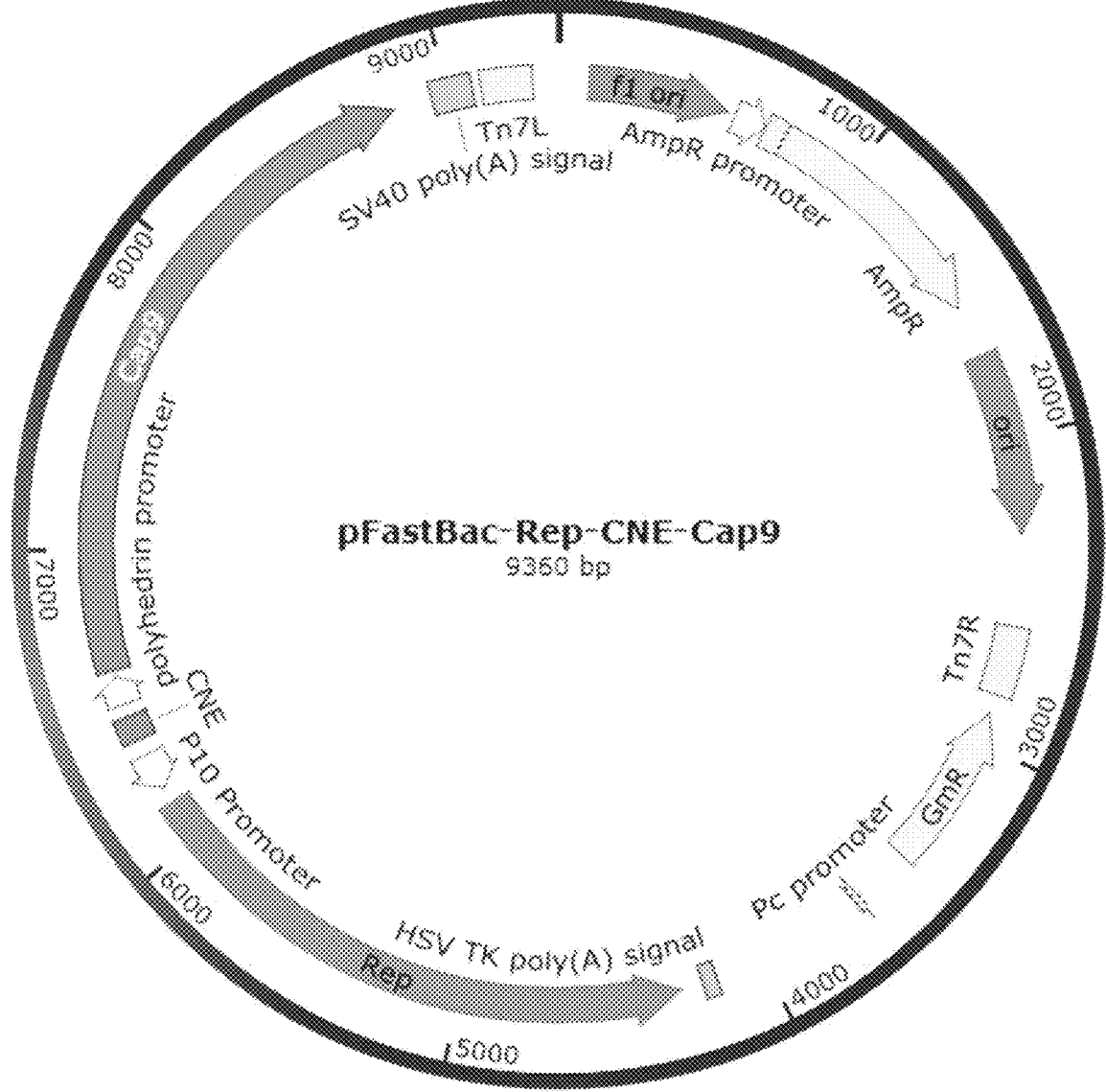
FIG. 4 is a schematic diagram of an rBV transfer vector pFastBac-Rep-CNE-Cap9 constructed in Example 2 of the present disclosure.

A recombinant transfer vector carrying a CNE sequence and Cap and Rep expression cassettes of AAV was constructed. A CNE sequence (SEQ ID NO: 5) was first amplified from a baculovirus genome through PCR and then inserted into the pFastBac-Rep-Cap9 vector through enzyme digestion and enzyme ligation to obtain a recombinant transfer vector pFastBac-Rep-CNE-Cap9, as shown in FIG. 4.

Figure 5:
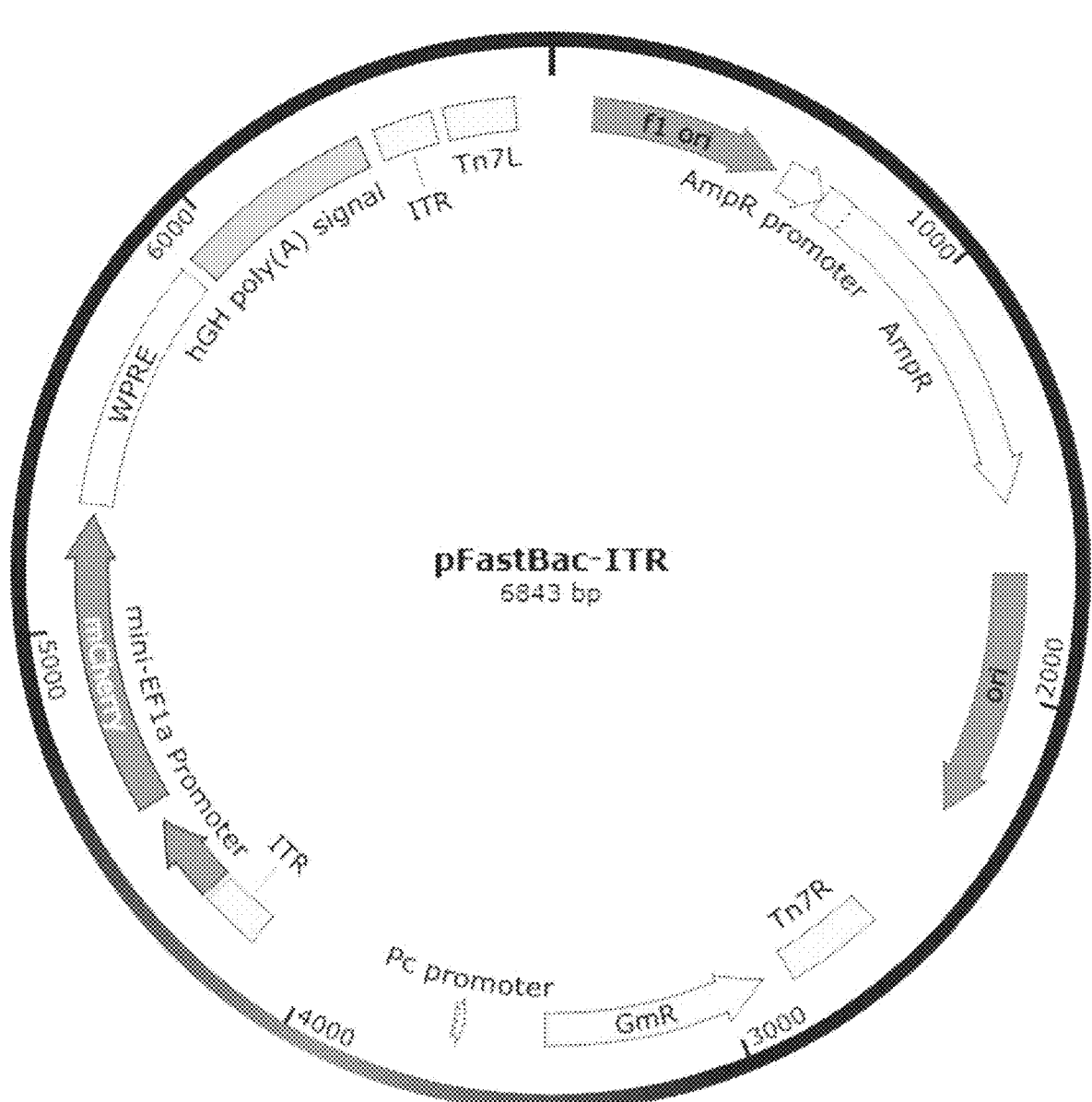
FIG. 5 is a schematic diagram of an rBV transfer vector pFastBac-ITR constructed in Example 2 of the present disclosure.

A recombinant transfer vector carrying an ITR core element (ITR-GOI) was constructed. A nucleotide sequence of the ITR-GOI was shown in SEQ ID NO: 6. In this example, GOI in the ITR core element adopted an RFP mcherry gene expression cassette, that is, the expression of mcherry was controlled by a miniEf1a promoter, which was convenient for the detection of an activity of rAAV. The ITR and the RFP expression cassette were constructed on a transfer vector pFastBac to obtain a recombinant transfer vector pFastBac-ITR, as shown in FIG. 5.

Figure 6:
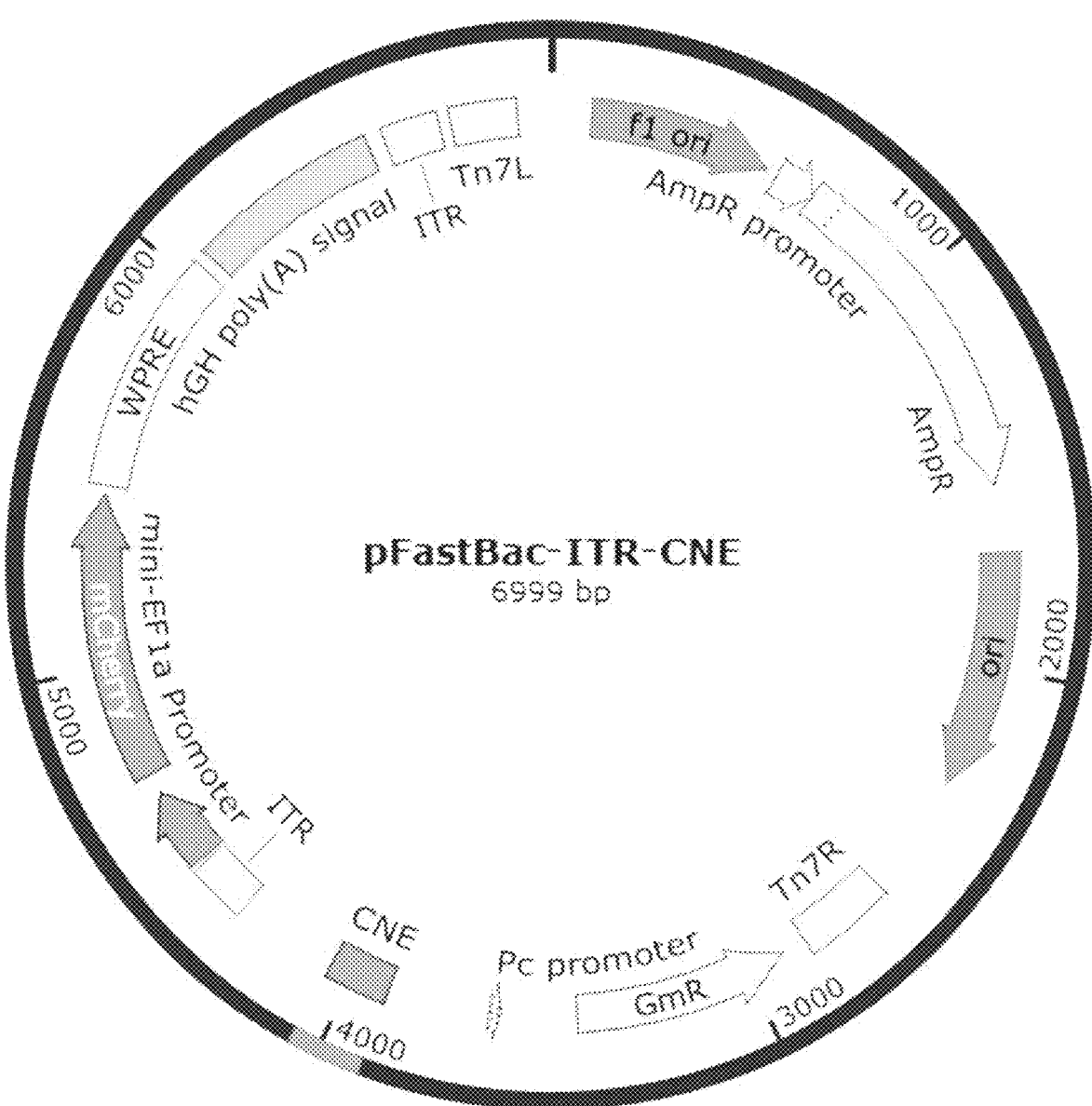
FIG. 6 is a schematic diagram of an rBV transfer vector pFastBac-ITR-CNE constructed in Example 2 of the present disclosure.

A transfer vector carrying a CNE sequence and ITR-GOI was constructed. A CNE sequence was first amplified from a baculovirus genome through PCR and then inserted into the pFastBac-ITR vector through enzyme digestion and enzyme ligation to obtain a recombinant transfer vector pFastBac-ITR-CNE, as shown in FIG. 6.

Figure 7:
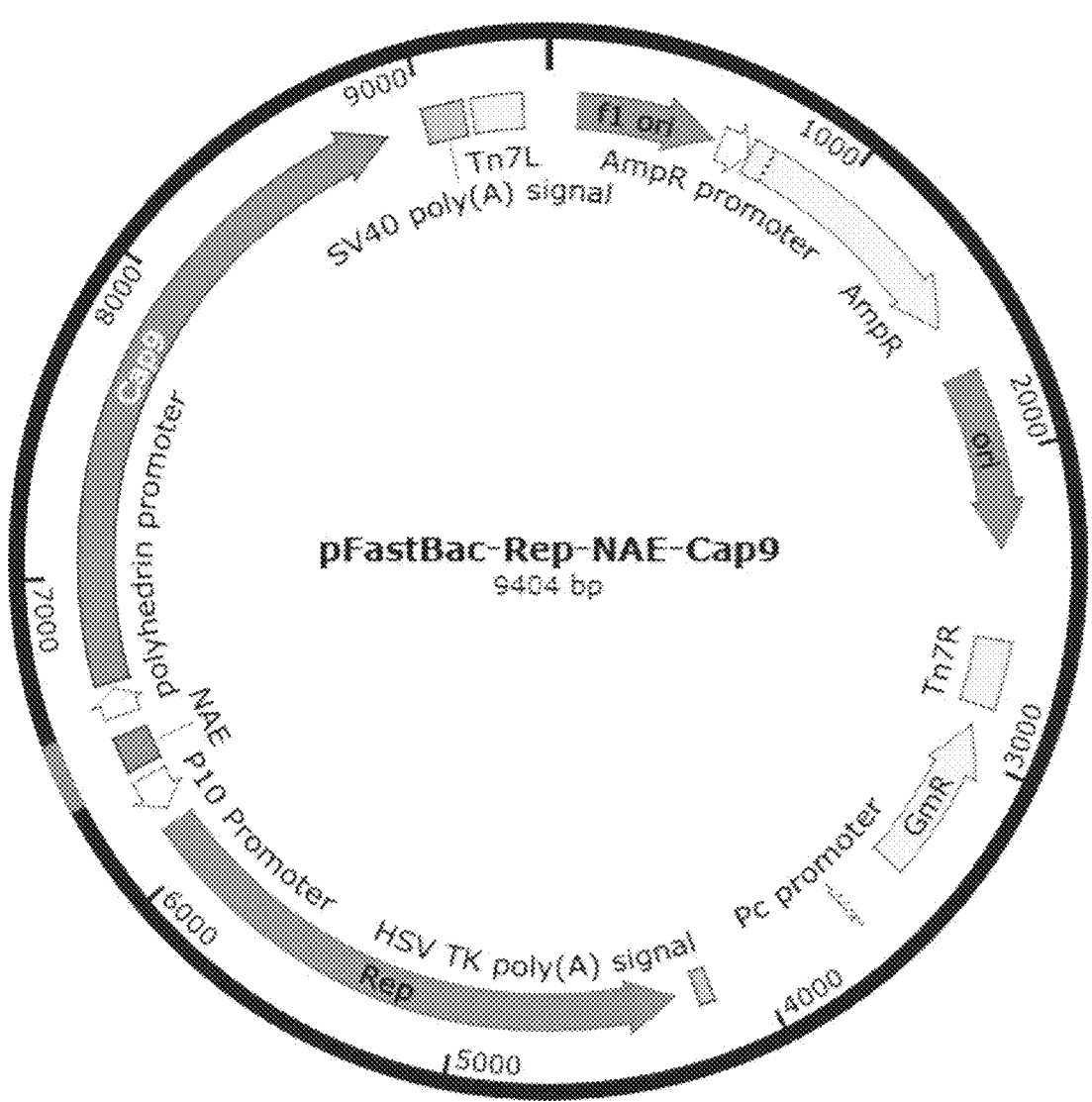
FIG. 7 is a schematic diagram of an rBV transfer vector pFastBac-Rep-NAE-Cap9 constructed in Example 3 of the present disclosure.

Example 3 Construction of Recombinant Transfer Vectors pFastBac-Rep-NAE-Cap9 and pFastBac-ITR-NAE that Include an NAE Sequence A recombinant transfer vector carrying an NAE sequence and Cap and Rep expression cassettes of AAV was constructed. An NAE sequence (SEQ ID NO: 7) was first amplified from a baculovirus genome through PCR and then inserted into the pFastBac-Rep-Cap9 vector constructed in Example 2 to obtain a recombinant transfer vector pFastBac-Rep-NAE-Cap9, as shown in FIG. 7.

Figure 8:
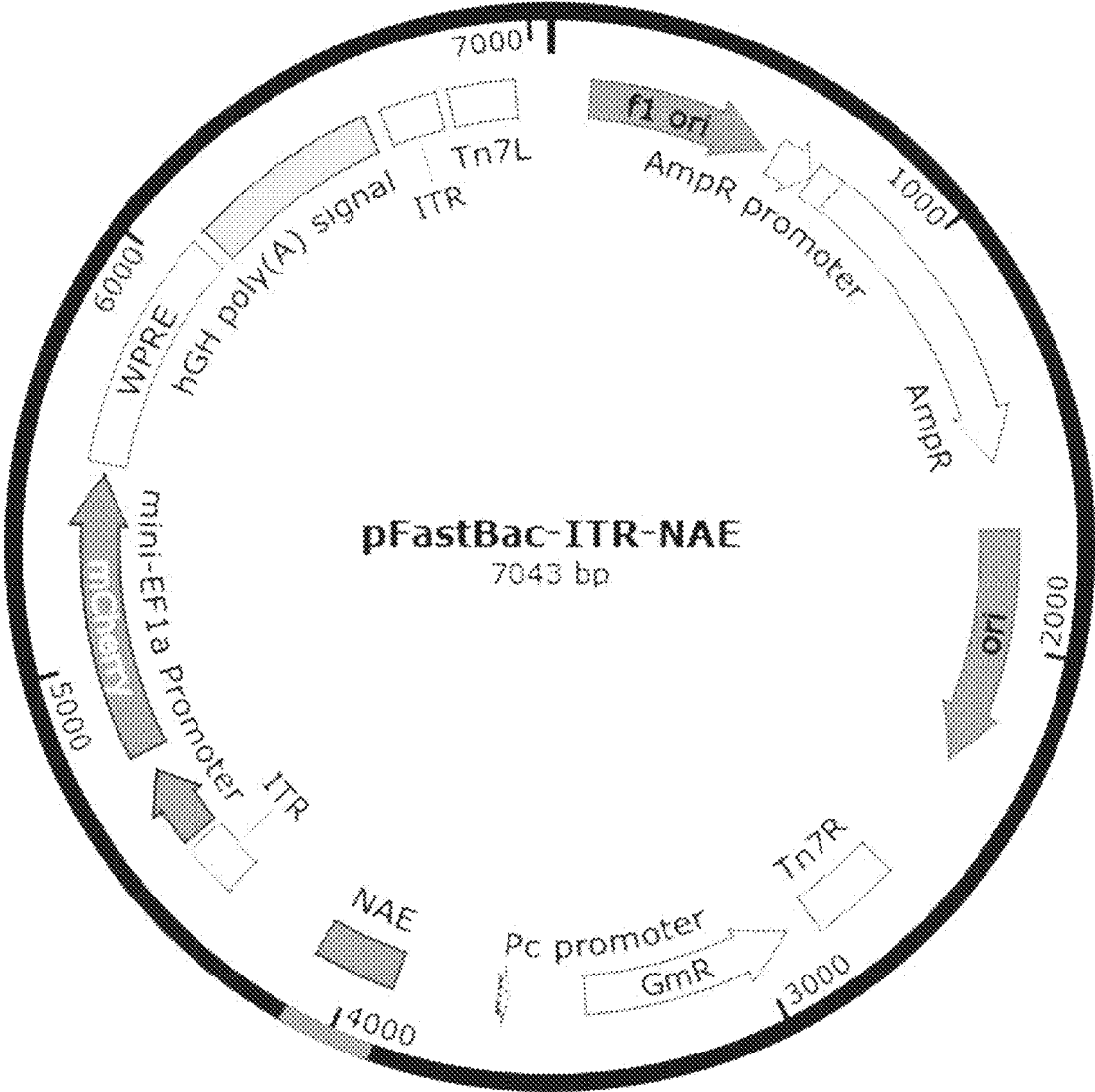
FIG. 8 is a schematic diagram of an rBV transfer vector pFastBac-ITR-NAE constructed in Example 3 of the present disclosure.

A transfer vector carrying an NAE sequence and ITR-GOI was constructed. An NAE sequence was first amplified from a baculovirus genome through PCR and then inserted into the pFastBac-ITR vector constructed in Example 2 through enzyme digestion and enzyme ligation to obtain a recombinant transfer vector pFastBac-ITR-NAE, as shown in FIG. 8.

Example 4 Construction of a Recombinant Bacmid with or without a CNE Sequence

The recombinant transfer vectors pFastBac-Rep-Cap9 and pFastBac-ITR obtained in Example 2 were transformed into a DH10Bac strain carrying a bacmid. The DH10Bac strain also included a helper plasmid (pMON7124 (13.2 kb), which had tetracycline resistance and could encode a transposase). Once the transfer vectors were transformed into the DH10Bac strain, Tn7 transposition occurred, and Rep-Cap9 and ITR sequences were cut off from the transfer vectors and inserted into the bacmid at a Tn7 site to produce recombinant bacmids Bac-Tn7-Rep-Cap9 and Bac-Tn7-ITR. A transposase required for the transposition was provided by the expression of the helper plasmid.

Similarly, the recombinant transfer vectors pFastBac-Rep-CNE-Cap9 and pFastBac-ITR-CNE obtained in Example 2 were transformed into a DH10Bac strain carrying a bacmid ΔCNE-Bac, and Tn7 transposition occurred to produce recombinant bacmids ΔCNE-Bac-Tn7-Rep-CNE-Cap9 and ΔCNE-Bac-Tn7-ITR-CNE.

Example 5 Construction of a Recombinant Bacmid with an NAE Sequence

With reference to Example 4, the recombinant transfer vectors pFastBac-Rep-NAE-Cap9 and pFastBac-ITR-NAE obtained in Example 3 were transformed into a DH10Bac strain carrying a bacmid ΔNAE-Bac, and Tn7 transposition occurred to produce recombinant bacmids ΔNAE-Bac-Tn7-Rep-NAE-Cap9 and ΔNAE-Bac-Tn7-ITR-NAE.

Example 6 Production of rBV with the Recombinant Bacmids Obtained in Examples 4 and 5 and Verification of Stability of the rBV with the CNE or NAE Sequence During Passages In order to further analyze the stability of the rBV with the CNE or NAE sequence during passages, titers of rBV and rAAV were detected by the quantitative polymerase chain reaction (Q-PCR) method in this example and the following examples. The Q-PCR method was cited from the patent CN108699567A.

Preparation of rBVs: DNA was extracted from the recombinant bacmids constructed in Examples 4 and 5 and then transfected into Sf9 insect cells to prepare rBVs and rAAVs. BEVs were successfully produced in the transfected Sf9 insect cells, and the further infection of BEVs replicating and proliferating in large quantities led to an obvious cytopathic effect (CPE) of Sf9 cells. A culture supernatant of Sf9 cells undergoing CPE was collected, which included a large amount of BEV and was the 0th generation of BEV (BEV-P0). Sf9 cells carrying a large amount of rAAV were collected. Sf9 cells cultivated in a suspended state were infected with the prepared BEV-P0 at a multiplicity of infection (MOI=1). 72 h after the infection, a cell viability decreased to 50% or less, and a resulting cell culture was centrifuged at 1,000 g for 5 min to obtain a culture supernatant and a cell pellet. The culture supernatant was denoted as the 1st generation BEV (BEV-P1), and the cell pellet was denoted as BEV-P0-packed rAAV The rBV prepared in this example was continuously passaged with a same MOI and then used to infect Sf9 cells to obtain P3, P4, P5 . . . P10 BEVs, and the stability of the rBV during passages was tested. Titers of all generations of BEV were determined by Q-PCR, and the titers were expressed in a unit of VG/mL (VG, virus genomes). A total titer of baculoviruses was determined with a pair of Q-PCR primers (Q-GP64-F: AACTTGGACATTACCCCGCC, as shown in SEQ ID NO: 8 and Q-GP64-R: CCGTTGTACG-CATACGCCTG, as shown in SEQ ID NO: 9) corresponding to the gp64 gene (present in all rBVs of the present disclosure). A titer of a baculovirus carrying the rep gene expression cassette and the cap gene expression cassette was determined with a pair of Q-PCR primers (Q-Rep-F: GAACAAGGTGGTGGACGAGT, as shown in SEQ ID NO: 10 and Q-Rep-R: ATTCAAACAGGCGCTTAAAT, as shown in SEQ ID NO: 11) corresponding to the rep gene. A titer of a baculovirus carrying ITR-GOI was determined with a pair of Q-PCR primers (Q-Tn7-F: TCGTATTAGCT-TACGACGCTACA, as shown in SEQ ID NO: 12 and Q-Tn7-R: TAGTTGGGGAACTGGGAGGGG, as shown in SEQ ID NO: 13) corresponding to the Tn7 sequence. The stability of an exogenous fragment (namely, the rep/cap gene expression cassette and ITR-GOI element) in BEV during passages was evaluated through ratios of Tn7/GP64 and REP/GP64. If the ratios remain stable, it indicates that the stability of the rep/cap gene expression cassette and ITR-GOI element during passages is prominent. If the ratios decrease significantly with the increase of passages, it indicates that the stability of the inserted exogenous fragment is poor. Throughout a passage process, a total BEV titer, namely, a Q-PCR titer of GP64, was used to calculate an MOI for passage.

Figure 9:
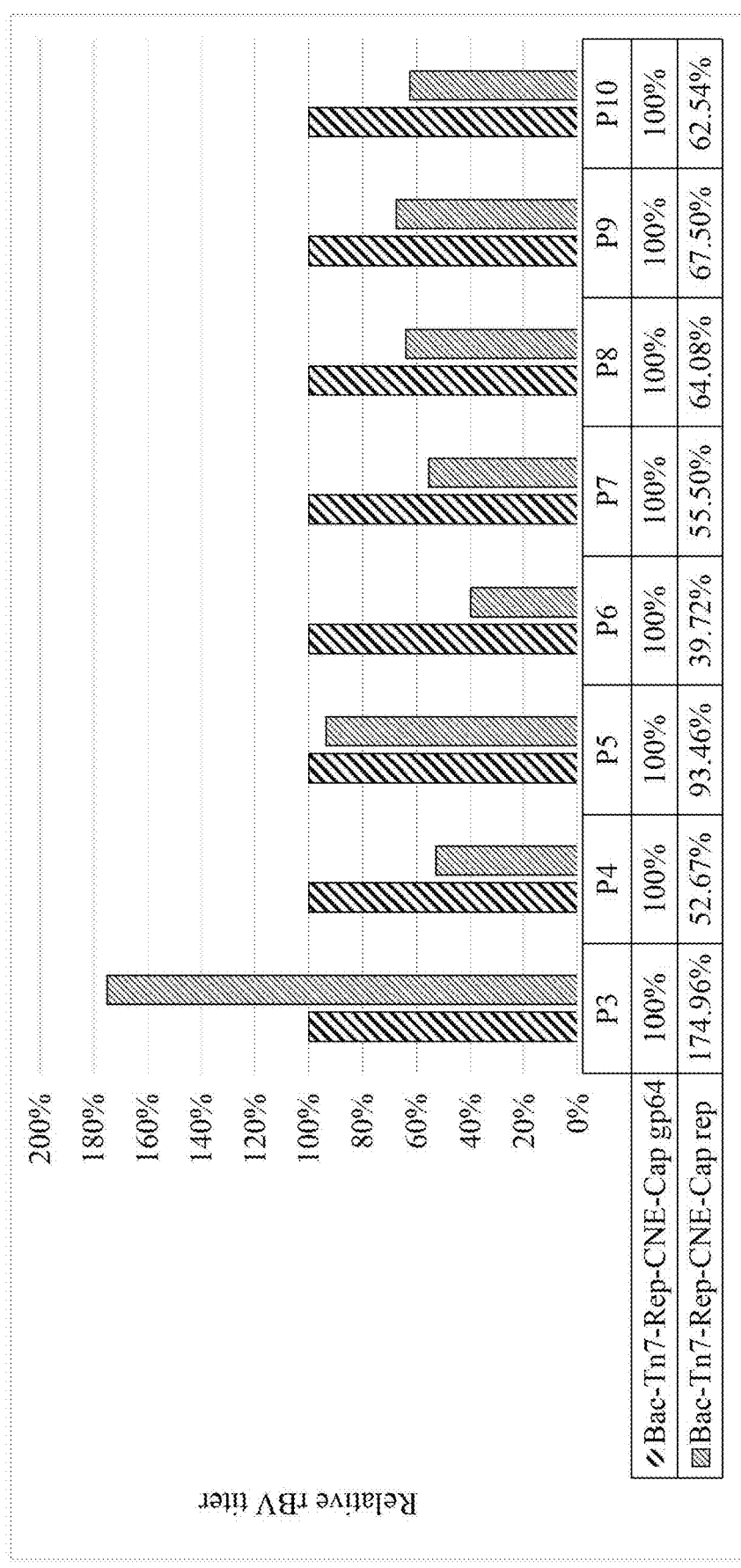
FIG. 9 shows titers of the 3rd generation to the 10th generation of recombinant baculovirus (rBV) carrying a Rep-CNE-Cap9 sequence in Example 6 of the present disclosure.
Figure 10:
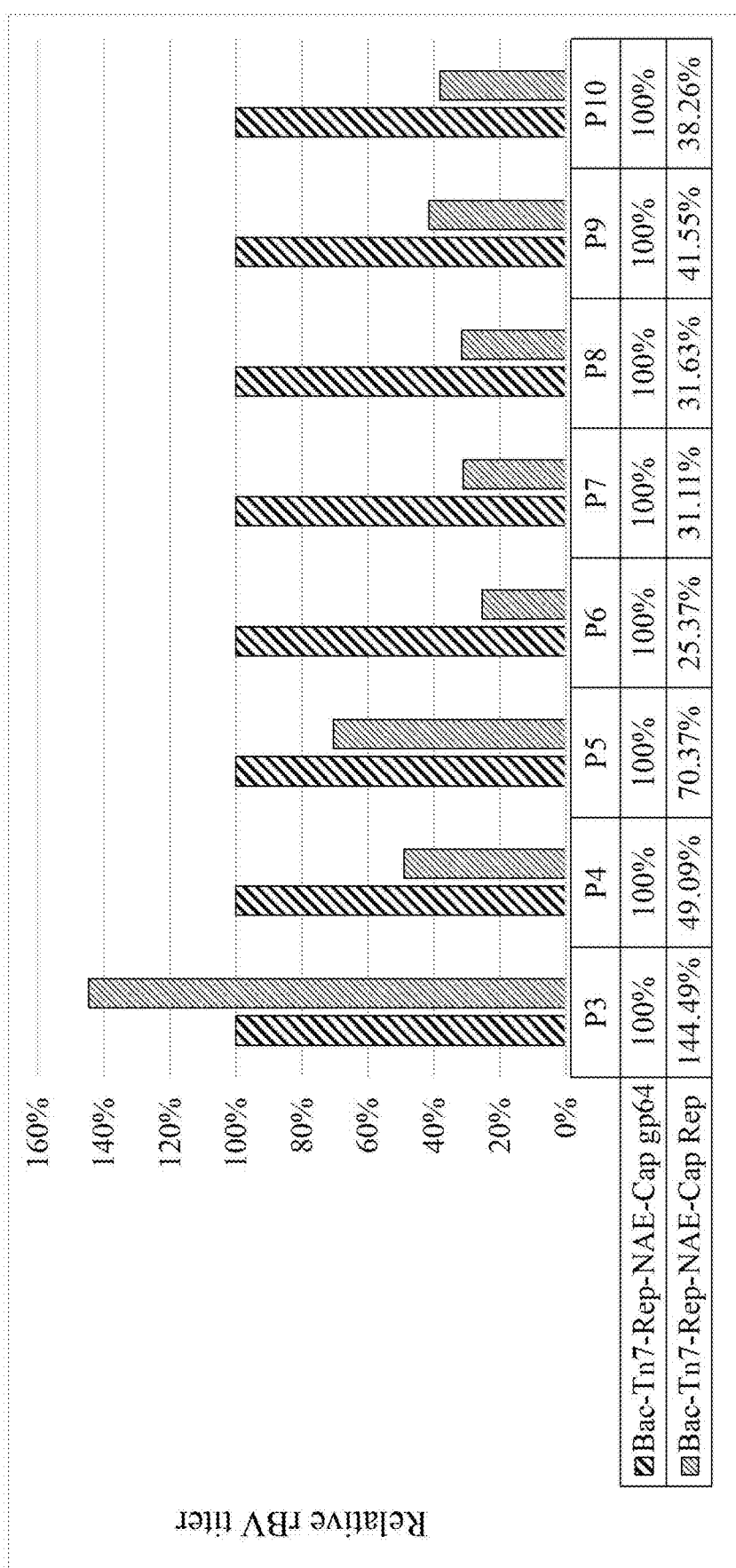
FIG. 10 shows titers of the 3rd generation to the 10th generation of recombinant baculovirus (rBV) carrying a Rep-NAE-Cap9 sequence in Example 6 of the present disclosure.
Figure 11:
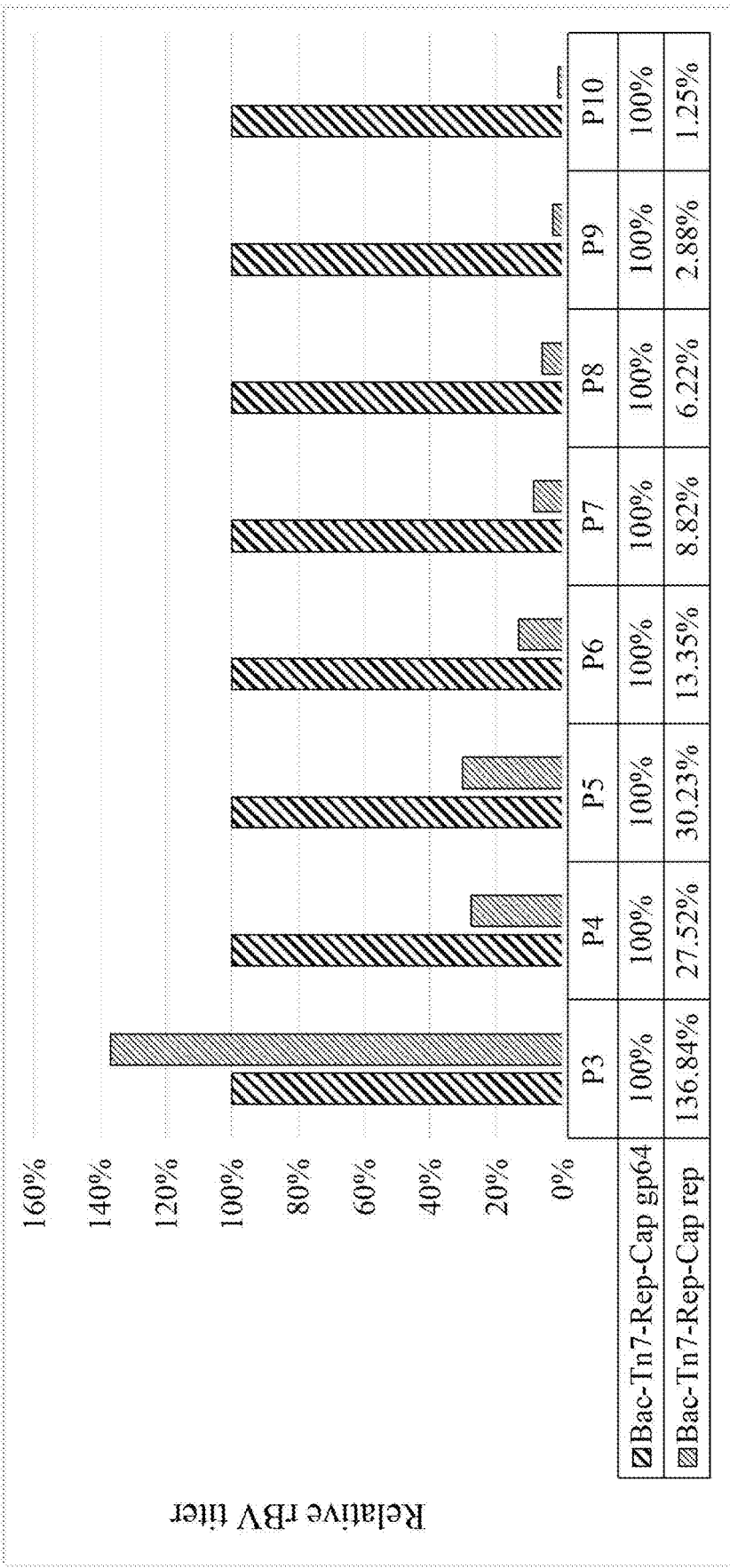
FIG. 11 shows titers of the 3rd generation to the 10th generation of recombinant baculovirus (rBV) carrying a Rep-Cap9 sequence without CNE or NAE in Example 6 of the present disclosure.
Figure 12:
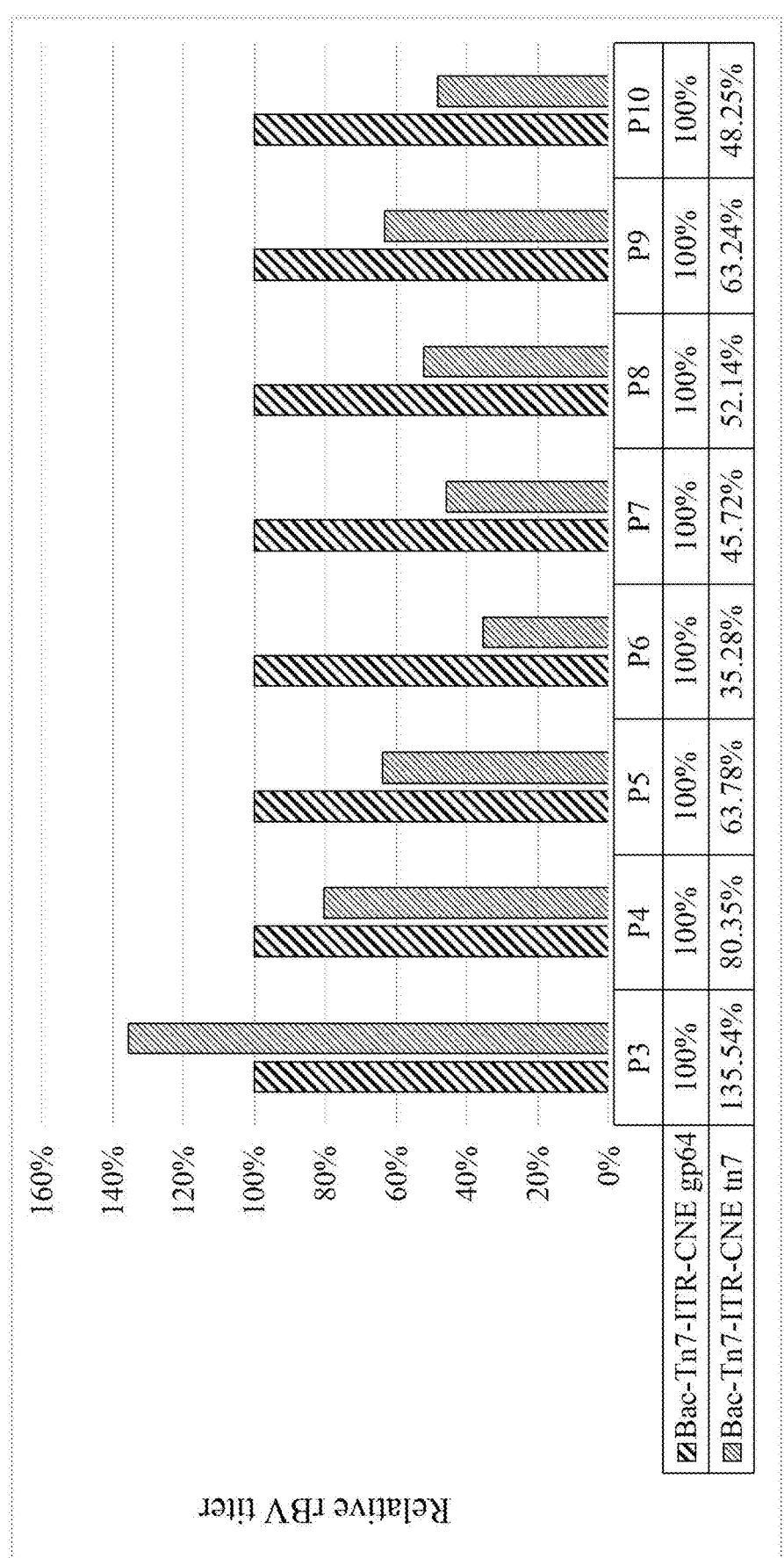
FIG. 12 shows titers of the 3rd generation to the 10th generation of recombinant baculovirus (rBV) carrying an ITR-CNE sequence in Example 6 of the present disclosure.
Figure 13:
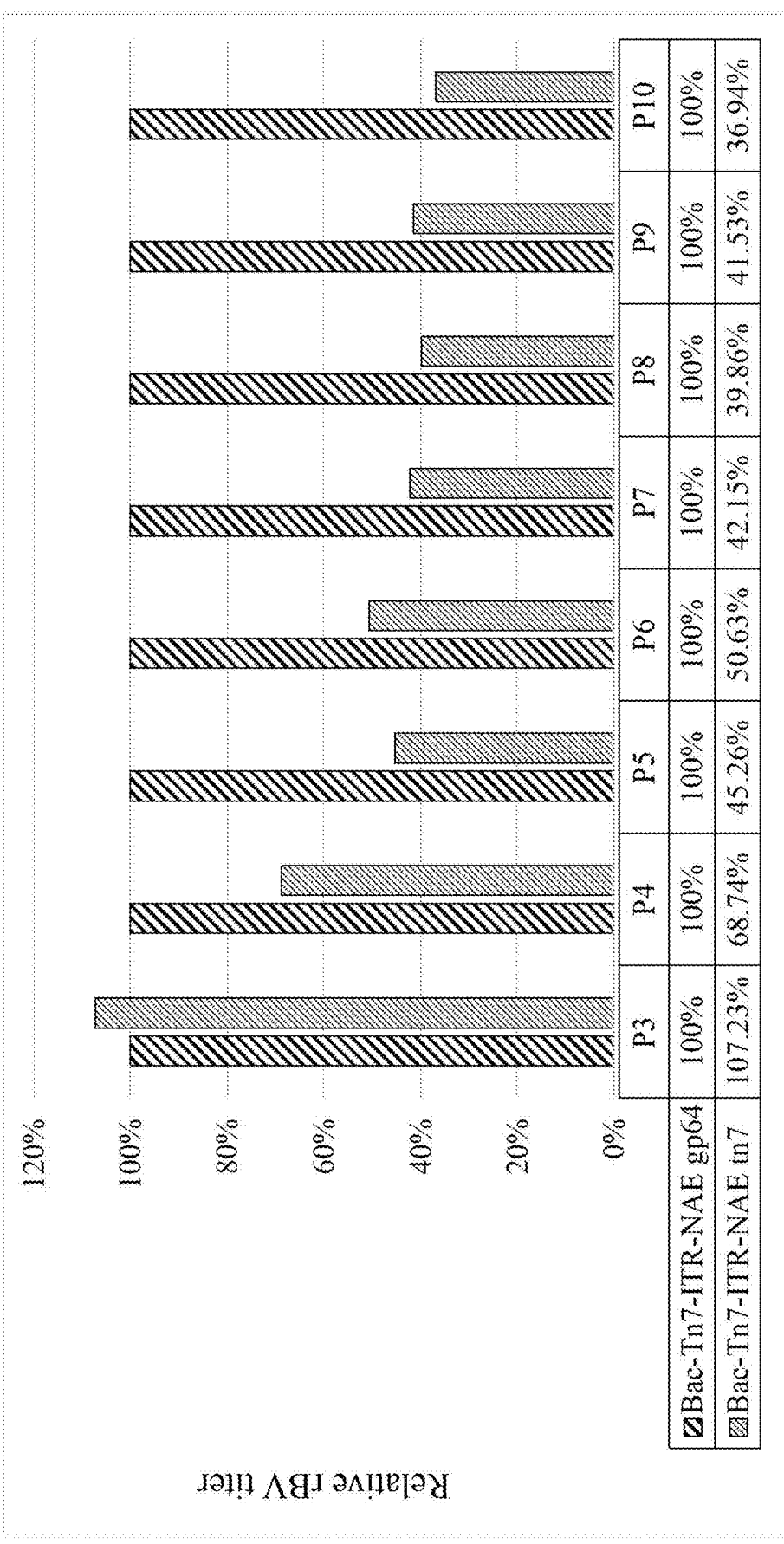
FIG. 13 shows titers of the 3rd generation to the 10th generation of recombinant baculovirus (rBV) carrying an ITR-NAE sequence in Example 6 of the present disclosure.
Figure 14:
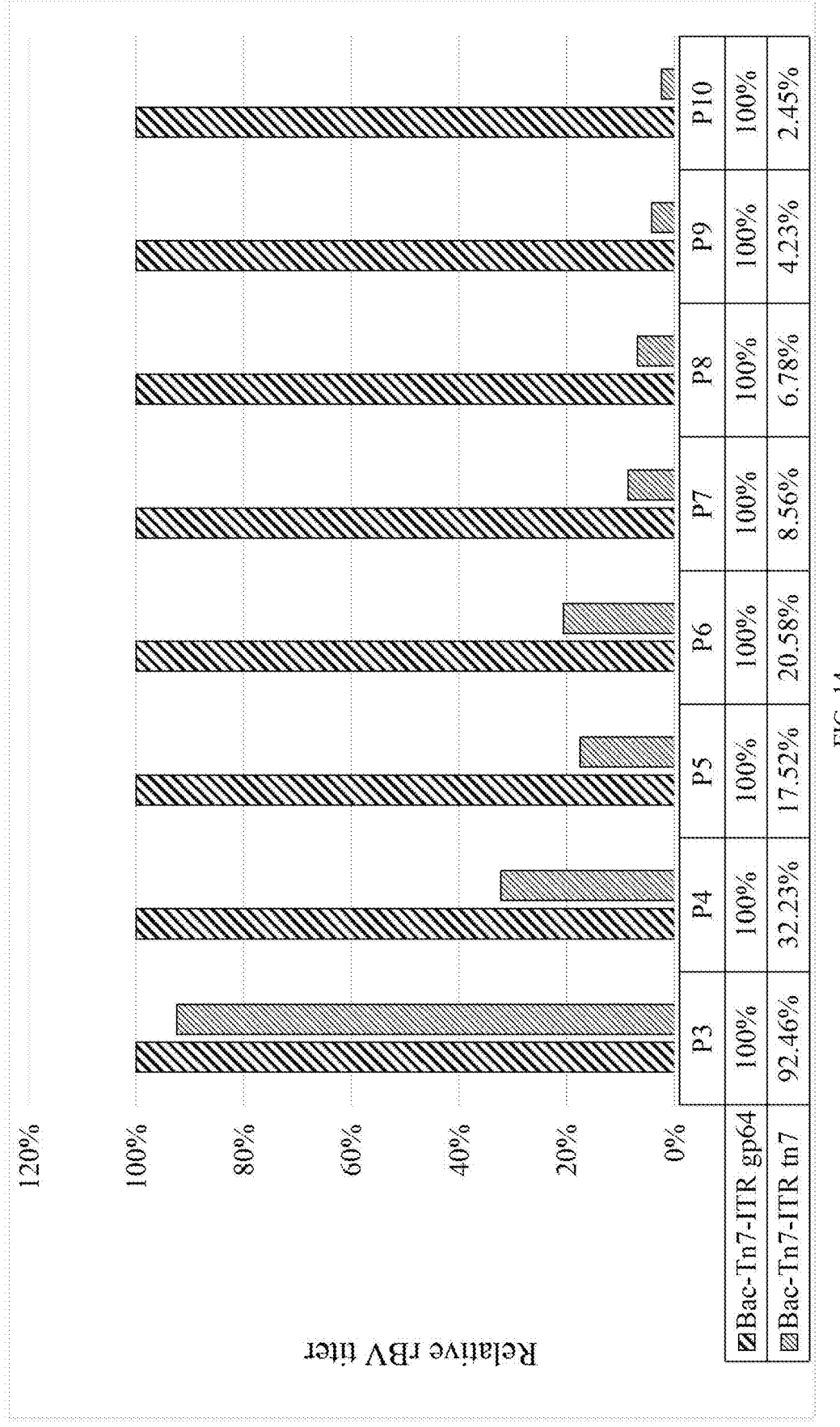
FIG. 14 shows titers of the 3rd generation to the 10th generation of recombinant baculovirus (rBV) carrying an ITR sequence without CNE or NAE in Example 6 of the present disclosure.

Experimental results of titers of the 3rd to 10th generations of rBVs with and without the CNE or NAE sequence are shown in FIG. 9 to FIG. 14: FIG. 9 shows the relative rBV titers in a host cell that is transfected with the recombinant bacmid ΔCNE-Bac-Tn7-Rep-CNE-Cap9 carrying the CNE sequence and continuously passaged to the 10th generation, where the relative rBV titers are determined with gp64 and rep qPCR primers. FIG. 10 shows the relative rBV titers in a host cell that is transfected with the recombinant bacmid ΔNAE-Bac-Tn7-Rep-NAE-Cap9 carrying the NAE sequence and continuously passaged to the 10th generation, where the relative rBV titers are determined with gp64 and rep qPCR primers. FIG. 11 shows the relative rBV titers in a host cell that is transfected with the recombinant bacmid Bac-Tn7-Rep-Cap9 without the CNE or NAE sequence and continuously passaged to the 10th generation, where the relative rBV titers are determined with gp64 and rep qPCR primers. FIG. 12 shows the relative rBV titers in a host cell that is transfected with the recombinant bacmid ΔCNE-Bac-Tn7-ITR-CNE carrying the CNE sequence and continuously passaged to the 10th generation, where the relative rBV titers are determined with gp64 and tn7 qPCR primers. FIG. 13 shows the relative rBV titers in a host cell that is transfected with the recombinant bacmid ΔNAE-Bac-Tn7-ITR-NAE carrying the NAE sequence and continuously passaged to the 10th generation, where the relative rBV titers are determined with gp64 and tn7qPCR primers. FIG. 14 shows the relative rBV titers in a host cell that is transfected with the recombinant bacmid Bac-Tn7-ITR without the CNE or NAE sequence and continuously passaged to the 10th generation, where the relative rBV titers are determined with gp64 and tn7 qPCR primers.

The above experimental data shows that, when an rBV vector does not include the CNE or NAE sequence, a titer of the specific rBV decreases rapidly with the increase of passages. A titer of the specific rBV of the p10 generation is less than 10% of a total rBV titer (FIG. 11 and FIG. 14). When an rBV vector includes the CNE or NAE sequence, a titer of the specific rBV does not decrease significantly with the increase of passages, and can remain relatively stable. A titer of the specific rBV is not less than 30% of a total rBV titer (FIG. 9, FIG. 10, FIG. 12, and FIG. 13).

Example 7 Detection of rAAV Yields of Different Generations of rBV Carrying the Rep Gene Expression Cassette and the Cap Gene Expression Cassette of AAV Another aspect of assessing the stability of rBV during passages was to detect a packaging rate and a supernatant titer of rAAV. Titers of all generations of rAAV were determined by Q-PCR, and the titers were expressed in a unit of VG/L (VG, virus genomes). The rAAV titer was detected with a pair of primers targeting the ITR sequence (Q-ITR-F: GGAACCCCTAGTGATGGAGTT, as shown in SEQ ID NO: 14 and Q-ITR-R: CGGCCTCAGTGAGCGA, as shown in SEQ ID NO: 15) or a pair of primers targeting the WPRE sequence (Q-WPRE-F: CCGTTGTCAGGCAACGTG, as shown in SEQ ID NO: 16 and Q-WPRE-R: AGCTGACAGGTGGTGGCAAT, as shown in SEQ ID NO: 17). In this example, the 3rd to 10th generations of rBV carrying the CNE sequence (ΔCNE-Bac-Tn7-Rep-CNE-Cap9), rBV carrying the NAE sequence (ΔNAE-Bac-Tn7-Rep-NAE-Cap9), and rBV carrying the ITR-GOI element (Bac-Tn7-ITR) were used to co-infect Sf9 cells to produce AAV vectors, and the 3rd to 10th generations of rBV without the CNE or NAE sequence (Bac-Tn7-Rep-Cap9) and rBV carrying the ITR-GOI element (Bac-Tn7-ITR) were used to co-infect Sf9 cells to produce AAV vectors. 3 d after viral infection, a cell pellet was collected, and an AAV yield was determined.

Figure 15:
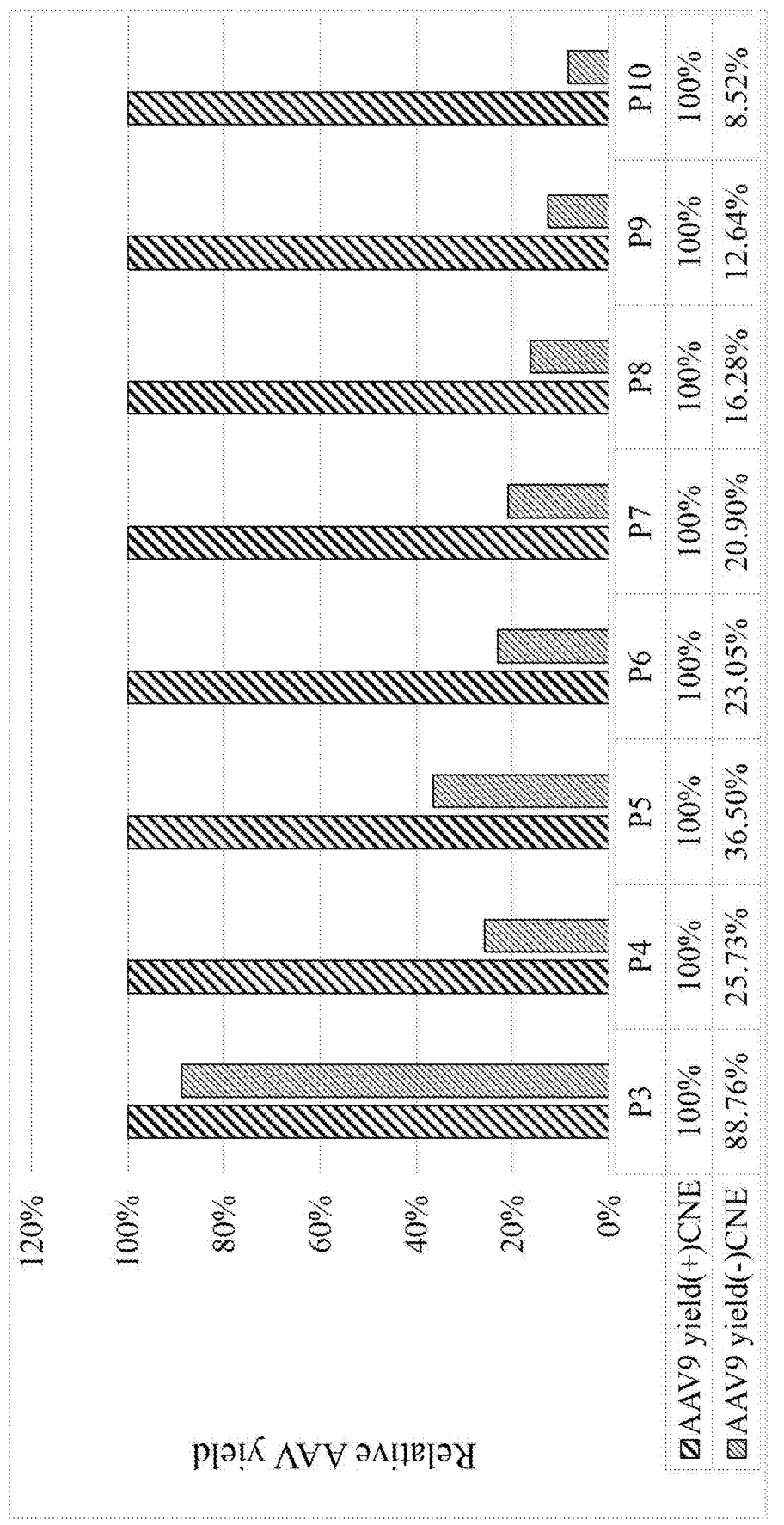
FIG. 15 is a comparison diagram of AAV yields of the 3rd generation to the 10th generation of recombinant baculovirus (rBV) with or without a CNE sequence in Example 7 of the present disclosure.
Figure 16:
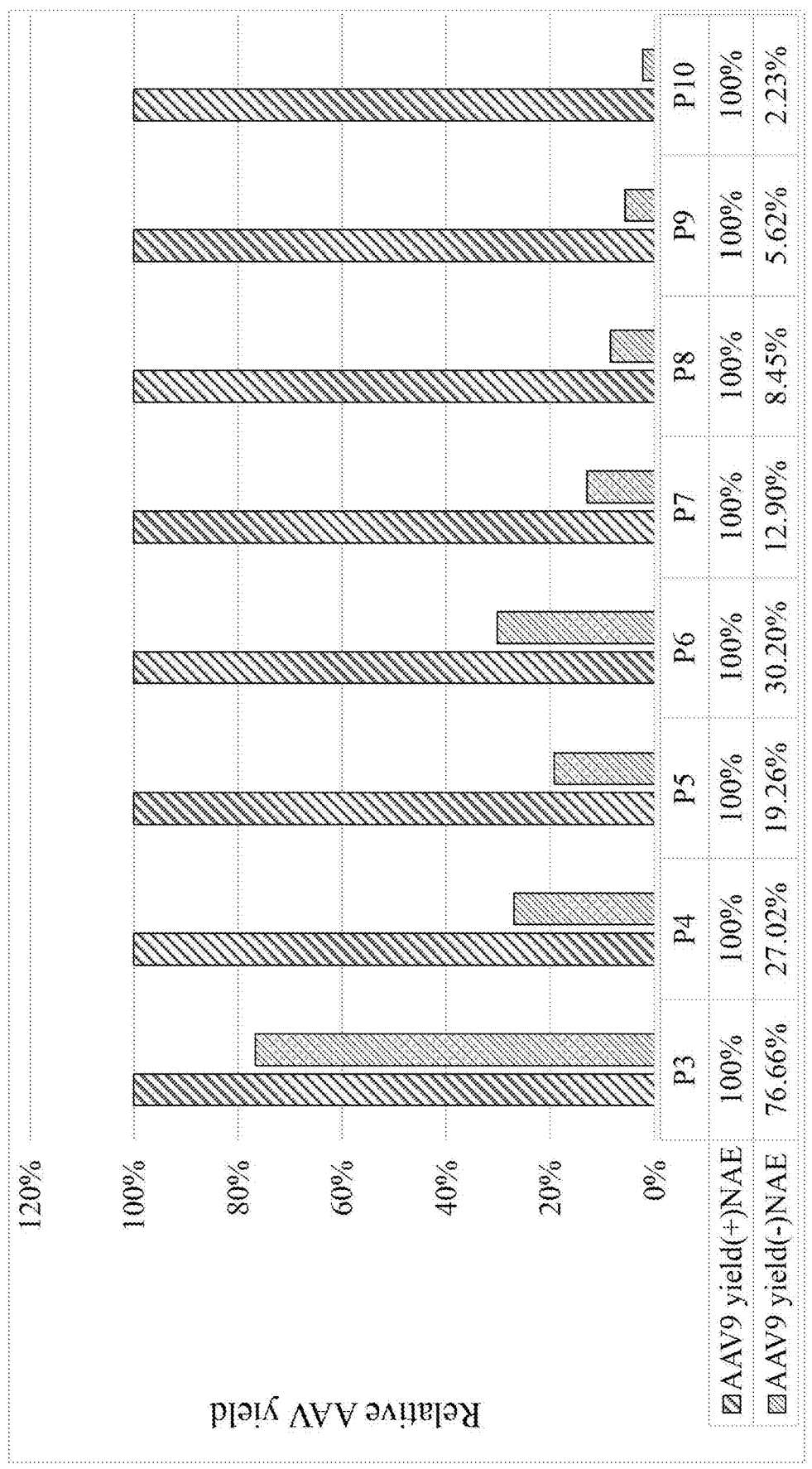
FIG. 16 is a comparison diagram of AAV yields of the 3rd generation to the 10th generation of recombinant baculovirus (rBV) with or without an NAE sequence in Example 7 of the present disclosure.

Experimental results are shown in FIG. 15 and FIG. 16. When an rBV vector includes the CNE or NAE sequence, a yield of AAV9 in a host cell remains stable from the 3rd to 10th generations. On the contrary, when an rBV vector does not include the CNE or NAE sequence, a yield of AAV9 decreases rapidly from the 3rd to 10th generations. This example shows that the CNE or NAE sequence enhances the stability of rAAV production of the rBV carrying the rep gene expression cassette and the cap gene expression cassette of AAV during continuous passages.

Figure 17:
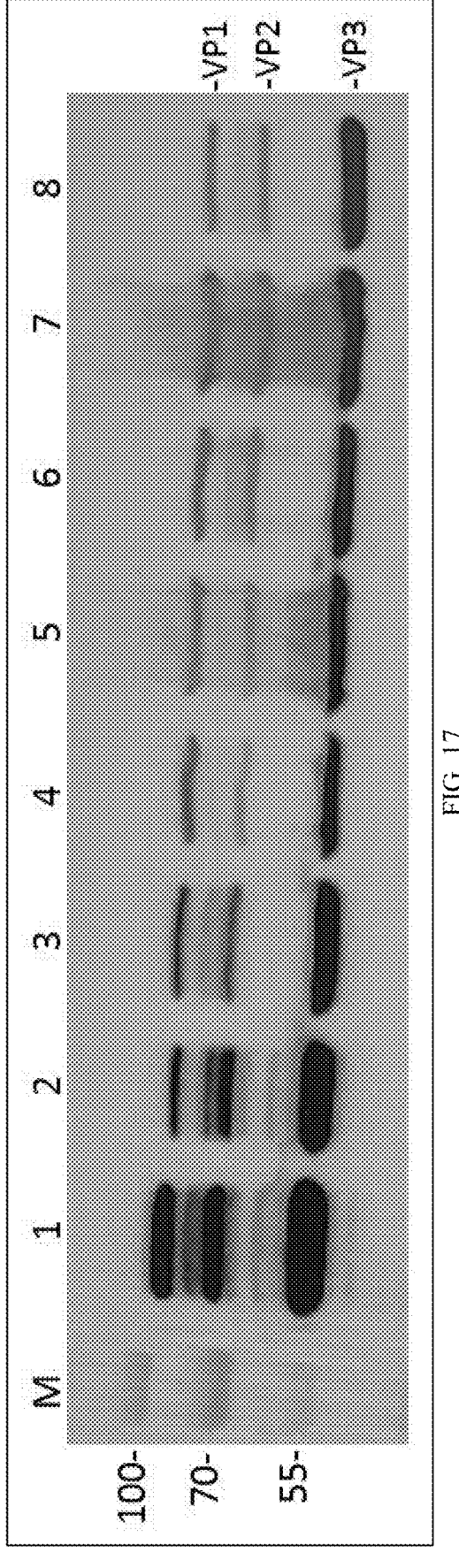
FIG. 17 is a Western blot pattern of expression of AAV capsid proteins in host cells infected with recombinant baculovirus (rBV) carrying a CNE sequence in Example 8 of the present disclosure.
Figure 18:
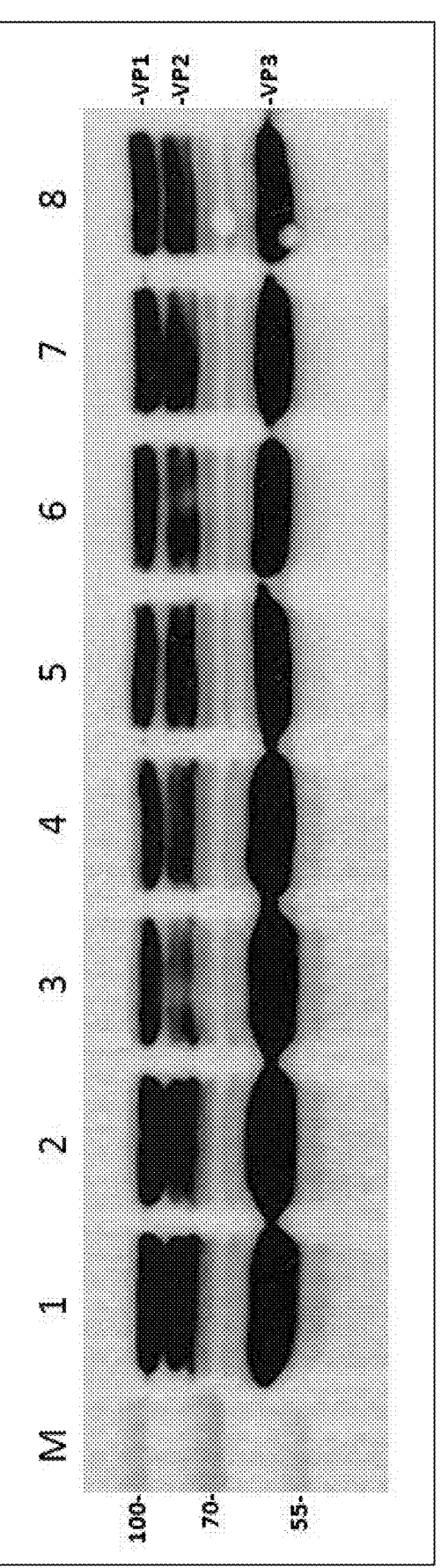
FIG. 18 is a Western blot pattern of expression of AAV capsid proteins in host cells infected with recombinant baculovirus (rBV) carrying an NAE sequence in Example 8 of the present disclosure.
Figure 19:
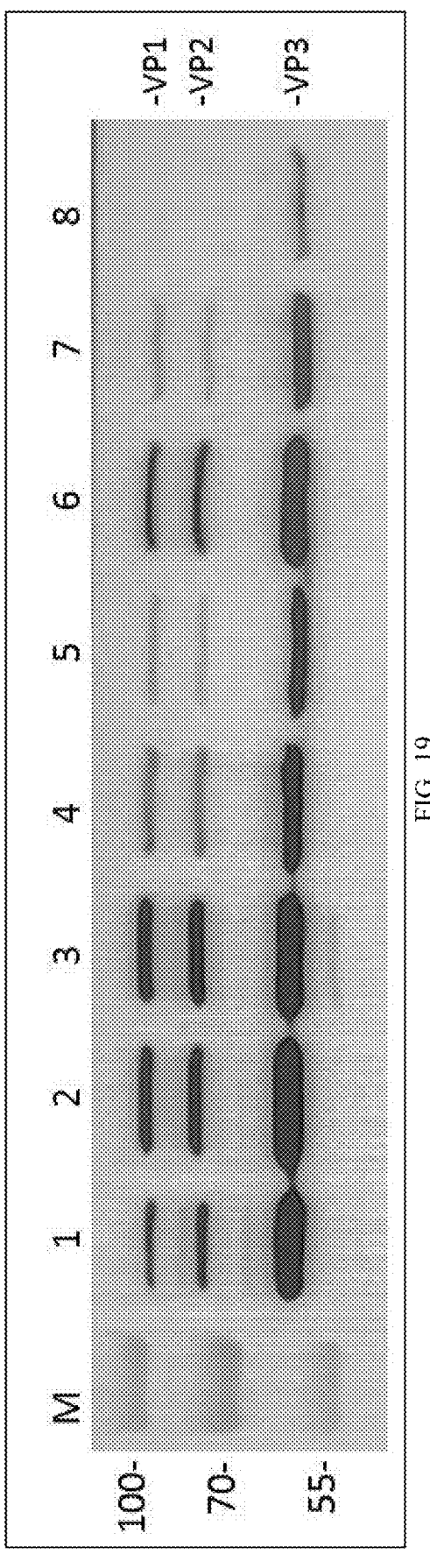
FIG. 19 is a Western blot pattern of expression of AAV capsid proteins in host cells infected with recombinant baculovirus (rBV) not carrying a CNE or NAE sequence in Example 8 of the present disclosure.

Example 8 Detection of Protein Expression Levels of Different Generations of rBV Carrying the Rep Gene Expression Cassette and the Cap Gene Expression Cassette of AAV In this example, expression levels of a Rep protein and a Cap protein were analyzed by Western Blot. FIG. 17 shows the expression of capsid proteins VP1, VP2, and VP3 in Sf9 cells infected with the 3rd to 10th generations of the rBV ΔCNE-Bac-Tn7-Rep-CNE-Cap9 carrying CNE. FIG. 18 shows the expression of capsid proteins VP1, VP2, and VP3 in Sf9 cells infected with the 3rd to 10th generations of the rBV ΔNAE-Bac-Tn7-Rep-NAE-Cap9 carrying NAE. FIG. 19 shows the expression of capsid proteins VP1, VP2, and VP3 in Sf9 cells infected with the 3rd to 10th generations of the rBV Bac-Tn7-Rep-Cap9 without CNE or NAE. In these figures, M represents a protein size marker, and lanes 1 to 8 represent cell lysates prepared from Sf9 host cells infected with the 3rd to 10th generations of rBV, respectively.

Figure 20:
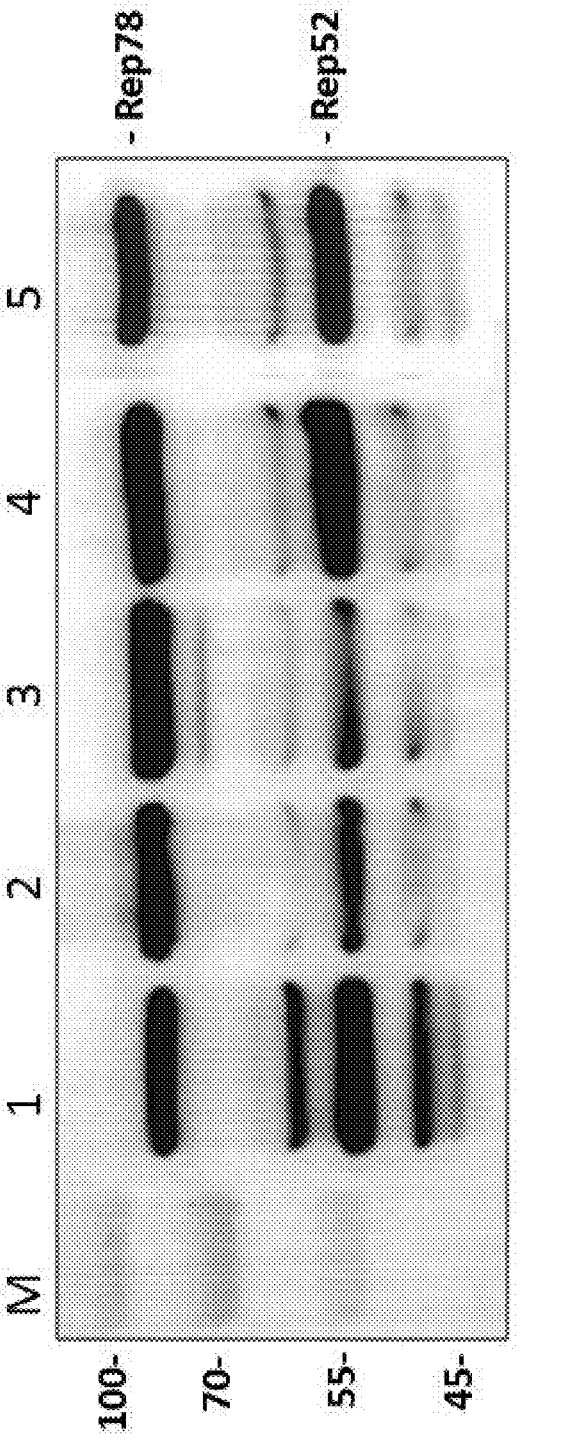
FIG. 20 is a Western blot pattern of expression of AAV Rep proteins in host cells infected with recombinant baculovirus (rBV) carrying a CNE sequence in Example 8 of the present disclosure.
Figure 21:
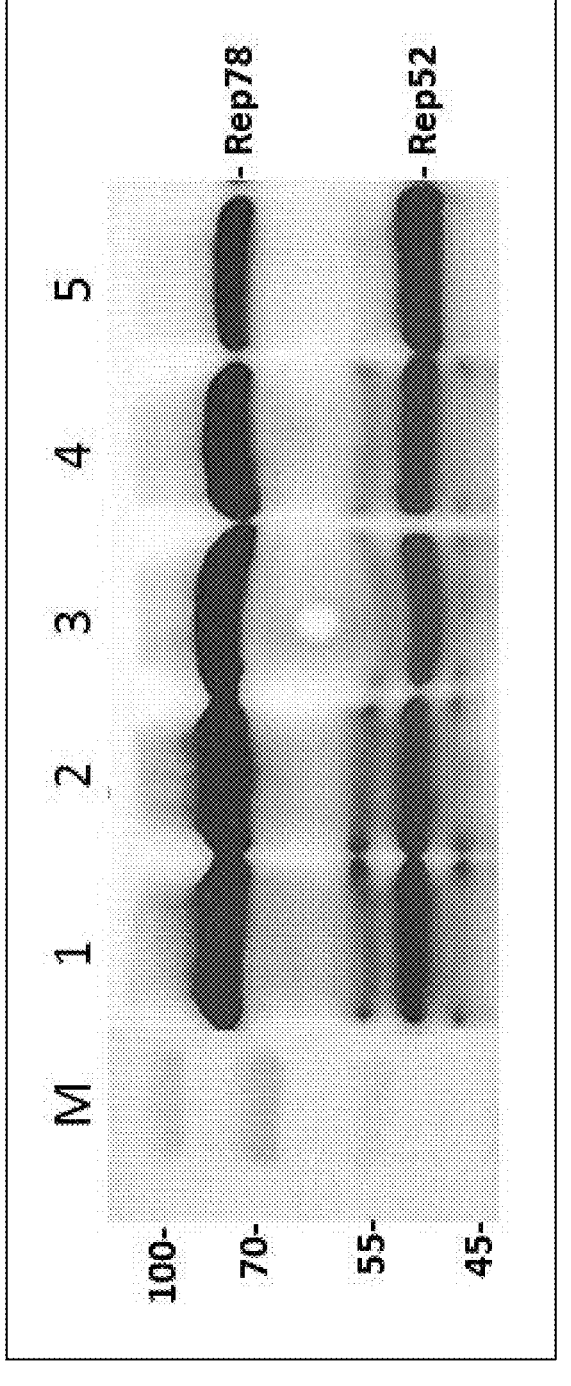
FIG. 21 is a Western blot pattern of expression of AAV Rep proteins in host cells infected with recombinant baculovirus (rBV) carrying an NAE sequence in Example 8 of the present disclosure.
Figure 22:
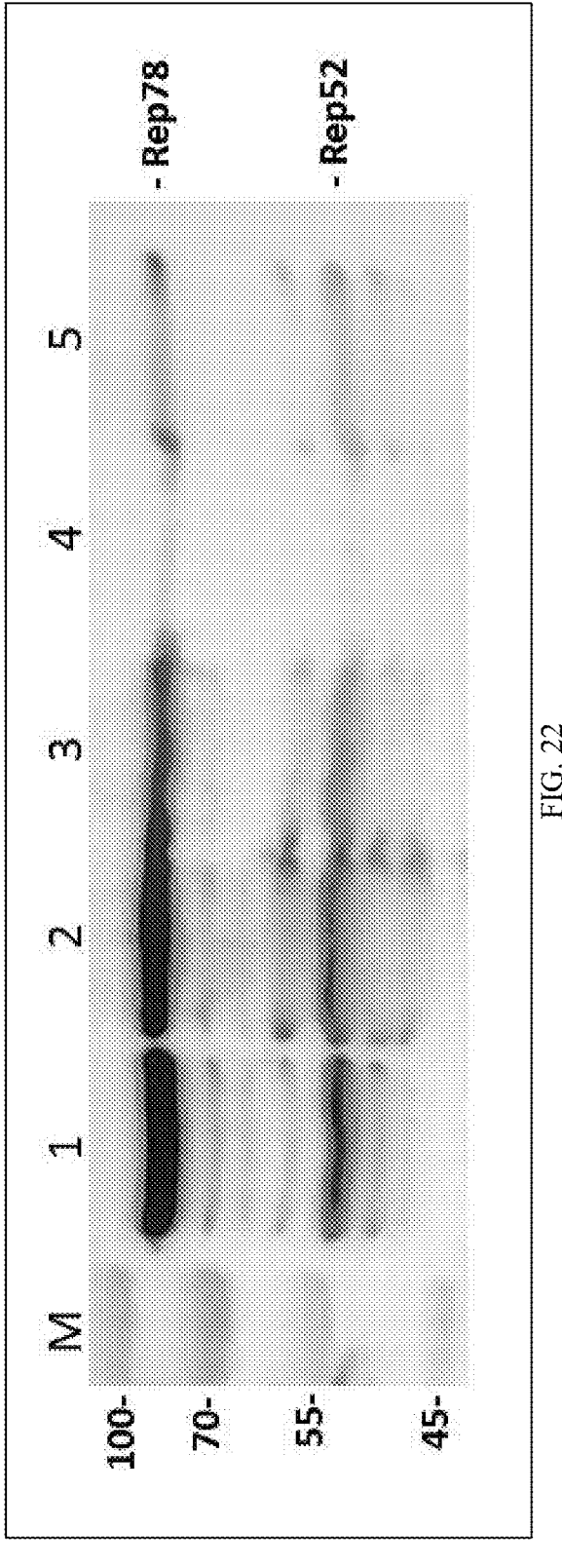
FIG. 22 is a Western blot pattern of expression of AAV Rep proteins in host cells infected with recombinant baculovirus (rBV) not carrying a CNE or NAE sequence in Example 8 of the present disclosure.

FIG. 20 shows the expression of proteins Rep78 and Rep52 in Sf9 cells infected with the 6th to 10th generations of the rBV ΔCNE-Bac-Tn7-Rep-CNE-Cap9 carrying CNE. FIG. 21 shows the expression of proteins Rep78 and Rep52 in Sf9 cells infected with the 6th to 10th generations of the rBV ΔNAE-Bac-Tn7-Rep-NAE-Cap9 carrying NAE. FIG. 22 shows the expression of proteins Rep78 and Rep52 in Sf9 cells infected with the 6th to 10th generations of the rBV Bac-Tn7-Rep-Cap9 without CNE or NAE. In these figures, M represents a protein size marker, and lanes 1 to 5 represent cell lysates prepared from Sf9 host cells infected with the 6th to 10th generations of rBV, respectively. The results in FIG. 17 to FIG. 22 show that rBV with the CNE or NAE sequence can express the VP and Rep proteins at higher levels than rBV without the CNE or NAE sequence during multiple passages.

It is easy for those skilled in the art to understand that the above-mentioned contents are merely the preferred examples of the present disclosure, and are not intended to limit the present disclosure. Any modifications, equivalent substitutions and improvements made within the spirit and principles of the present disclosure should fall within the protection scope of the present disclosure.

What is claimed is:

1. A recombinant baculovirus (rBV) shuttle vector for preparing a rBV, comprising an exogenous gene expression cassette and a stable sequence, wherein the stable sequence is a conserved noncoding element (CNE) sequence or a nucleocapsid assembly-essential element (NAE) sequence; the exogenous gene expression cassette is at least one of a cap gene expression cassette of an adeno-associated virus (AAV), a rep gene expression cassette of the AAV, and an AAV inverted terminal repeat (ITR) core expression element operably linked to a heterologous coding sequence; and the stable sequence is located at a site 5 kb or less from at least one of a start and a stop end of the cap gene expression cassette, a start and a stop end of the rep gene expression cassette, and two ends of the AAV ITR core expression element operably linked to the heterologous coding sequence.

2. The rBV shuttle vector according to claim 1, wherein the exogenous gene expression cassette is the AAV ITR core expression element operably linked to the heterologous coding sequence and the cap gene expression cassette.

3. The rBV shuttle vector according to claim 1, wherein the rBV shuttle vector is obtained by inserting the exogenous gene expression cassette and the stable sequence into a parental baculovirus shuttle vector at a transposon insertion site through rBV transfer vector-mediated Tn7 transposition, and when the stable sequence is a CNE sequence, the native CNE sequence or when the stable sequence is a NAE sequence, the native NAE sequence is absent in the parental baculovirus shuttle vector.

4. A method of preparing a rBV comprising a step of infecting the rBV shuttle vector according to claim 1 into an insect cell.

5. The method according to claim 4, wherein the exogenous gene expression cassette of the baculovirus shuttle vector is the AAV ITR core expression element operably linked to the heterologous coding sequence and the cap gene expression cassette.

6. The method according to claim 4, wherein the rBV shuttle vector is obtained by inserting the exogenous gene expression cassette and the stable sequence into a parental baculovirus shuttle vector at a transposon insertion site through rBV transfer vector-mediated Tn7 transposition, and when the stable sequence is a CNE sequence, the native CNE sequence or when the stable sequence is a NAE sequence, the native NAE sequence is absent in the parental baculovirus shuttle vector.

7. An insect cell comprising the rBV shuttle vector according to claim 1.

8. A method for in vitro production of rBV, comprising: cultivating the insect cell according to claim 7 to obtain the rBV.

9. The insect cell according to claim 7, wherein the exogenous gene expression cassette of the rBV shuttle vector is the AAV ITR core expression element operably linked to the heterologous coding sequence and the cap gene expression cassette.

10. The insect cell according to claim 7, wherein the rBV shuttle vector is obtained by inserting the exogenous gene expression cassette and the stable sequence into a parental baculovirus shuttle vector at a transposon insertion site through rBV transfer vector-mediated Tn7 transposition, and when the stable sequence is a CNE sequence, the native CNE sequence or when the stable sequence is a NAE sequence, the native NAE sequence is absent in the parental baculovirus shuttle vector.

11. The baculovirus shuttle vector according to claim 1, wherein the CNE sequence is the amino acid sequence of SEQ ID NO: 5; and the NAE sequence is the amino acid sequence of SEQ ID NO: 7.

12. A rBV shuttle vector for preparing a recombinant adeno-associated virus (rAAV), comprising an exogenous gene expression cassette and a stable sequence, wherein the stable sequence is a CNE sequence or a NAE sequence; the exogenous gene expression cassette is a cap gene expression cassette of an adeno-associated virus (AAV) and a rep gene expression cassette of the AAV; and the stable sequence is located between the cap gene expression cassette and the rep gene expression cassette, and the cap gene expression cassette and the rep gene expression cassette are in opposite directions, and starting ends of the cap gene expression cassette and the rep gene expression cassette are arranged oppositely and face towards the stable sequence; or the exogenous gene expression cassette is an AAV inverted terminal repeat (ITR) core expression element operably linked to a heterologous coding sequence functional gene; and the stable sequence is located at a site 5 kb or less from the two ends of the AAV ITR core expression element operably linked to the heterologous coding sequence.

13. The rBV shuttle vector according to claim 12, wherein the rAAV is obtained by inserting the exogenous gene expression cassette and the stable sequence into a parental baculovirus shuttle vector at a transposon insertion site through rBV transfer vector-mediated Tn7 transposition, and when the stable sequence is a CNE sequence, the native CNE sequence or when the stable sequence is a NAE sequence, the native NAE sequence is absent in the parental baculovirus shuttle vector.

14. A method of preparing a rAAV comprising a step of infecting the baculovirus shuttle vector according to claim 12 into an insect cell.

15. An insect cell comprising the rBV shuttle vector according to claim 12.

16. A method for in vitro production of rAAV, comprising: cultivating the insect cell according to claim 15 to obtain the rAAV.

17. The baculovirus shuttle vector according to claim 12, wherein the CNE sequence is the amino acid sequence of SEQ ID NO: 5; and the NAE sequence is the amino acid sequence of SEQ ID NO: 7.

* * * * *